(12) United States Patent
Gotoh et al.

(10) Patent No.: US 7,667,049 B2
(45) Date of Patent: Feb. 23, 2010

(54) PROCESS FOR PRODUCING 3,4-DISUBSTITUTED PYRROLIDINE DERIVATIVE AND PRODUCTION INTERMEDIATE THEREOF

(75) Inventors: Takayuki Gotoh, Tochigi (JP); Ichirou Araya, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 12/224,898

(22) PCT Filed: Mar. 8, 2007

(86) PCT No.: PCT/JP2007/054501

§ 371 (c)(1), (2), (4) Date: Sep. 9, 2008

(87) PCT Pub. No.: WO2007/102567

PCT Pub. Date: Sep. 13, 2007

(65) Prior Publication Data

US 2009/0023935 A1    Jan. 22, 2009

(30) Foreign Application Priority Data

Mar. 9, 2006   (JP) .............................. 2006-063591

(51) Int. Cl.
    *C07D 207/04*   (2006.01)
(52) U.S. Cl. ...................................... 548/566
(58) Field of Classification Search .............. None
    See application file for complete search history.

(56) References Cited

U.S. PATENT DOCUMENTS 7,153,851 B2    12/2006   Asahina et al.
2005/0182052 A1   8/2005   Asahina et al.
2006/0281779 A1   12/2006  Asahina et al.

FOREIGN PATENT DOCUMENTS

| JP | 2005-239617 | * | 9/2005 |
| WO | 03/078439 | | 9/2003 |
| WO | 2005/026147 | | 3/2005 |

OTHER PUBLICATIONS

Morissette et al. "High-throughput crystallization: polymorphs, salts, co-crystals and solvates of pharmaceutical solids." Advanced Drug Delivery Reviews 2004, 56, 275-300.*
Vippagunta, Sudha R. "Crystalline Solids." Advanced Drug Delivery Reviews 48(2001): 3-26.*
International Search Report issued May 29, 2007 in the International (PCT) Application PCT/JP2007/054501 of which the present application is the U.S. National Stage, abs only.

* cited by examiner

*Primary Examiner*—Rei-Tsang Shiao
*Assistant Examiner*—Alicia L Fierro
(74) *Attorney, Agent, or Firm*—Wenderoth, Lind & Ponack, L.L.P.

(57) ABSTRACT

An industrially advantageous process for the production of (3R,4S)-3-cyclopropylaminomethyl-4-fluoropyrrolidine or an enantiomer thereof that is useful as an intermediate for the production of novel antimicrobial agents 10-(3-cyclopropylaminomethyl-4-fluoropyrrolidinyl)pyridobenzoxazine carboxylic acid derivatives.

Highly stereoselective asymmetric hydrogenation of 1-protected-4-alkoxycarbonyl-3-oxopyrrolidine, followed by ester hydrolysis, followed by amidation with cyclopropylamine gives crude crystals. The crude crystals are purified by recrystallization to give a novel compound (3R,4S)-1-protected-3-cyclopropylcarbamoyl-4-hydroxypyrrolidine or an enantiomer thereof at high optical purity. The use of these intermediates enables industrial production of high-quality products of (3R,4S)-3-cyclopropylaminomethyl-4-fluoropyrrolidine or an enantiomer thereof. The process is highly simple and can produce the desired products at high purity and stable yields.

2 Claims, No Drawings

PROCESS FOR PRODUCING 3,4-DISUBSTITUTED PYRROLIDINE DERIVATIVE AND PRODUCTION INTERMEDIATE THEREOF

TECHNICAL FIELD

The present invention relates to a novel process for the production of optically active forms of 3-cyclopropylaminomethyl-4-fluoropyrrolidine, a compound useful as an intermediate for the production of 10-(3-cyclopropylaminomethyl-4-fluoropyrrolidinyl)pyridobenzoxazine carboxylic acid derivatives, antimicrobial agents that are not only safe and potent, but are also effective against drug-resistant bacteria that can hardly be killed by conventional antimicrobial agents. The present invention also relates to intermediates for the production of 3-cyclopropylaminomethyl-4-fluoropyrrolidine.

BACKGROUND ART

The applicant of the present application previously disclosed 10-(3-cyclopropylaminomethyl-4-fluoropyrrolidinyl)pyridobenzoxazine carboxylic acid derivatives as antimicrobial agents that are safe and effective against drug-resistant bacteria (Patent Document 1). This patent document describes a production process of 3-cyclopropylaminomethyl-4-fluoropyrrolidine that serves as a useful intermediate. Nonetheless, the process still had drawbacks that need to be addressed to make it ideal for mass-production and industrial use. The applicant later disclosed an improved process for synthesizing (3R,4S)-3-cyclopropylaminomethyl-4-fluoropyrrolidine (Patent Document 2). The process described in Patent Document 2 uses (3R,4R)-(1-benzyloxycarbonyl-4-hydroxypyrrolidine-3-yl)methano 1 as a starting material. In this process, the primary hydroxyl groups are first brominated and the secondary hydroxyl groups are subsequently fluorinated. The resulting product is then reacted with a cyclopropylamine derivative. Subsequent removal of the benzyloxycarbonyl protecting group gives the target product. Since all of the intermediates produced in this process are oil-like materials, the process requires frequent purification by silica gel column to purify these products. In addition, the introduction of the cyclopropylamine derivative requires an excess amount of cyclopropylamine and heating in an autoclave. Thus, the process is not favorable in terms of workability and cost and it has been difficult to implement this process on an industrial scale. In order to address these problems, there is a need to develop a production process suitable for practical production of the intermediate.

Patent Document 1: WO03/078439 pamphlet
Patent Document 2: Japanese Patent Application Laid-Open No. 2005-239617

DISCLOSURE OF THE INVENTION

Problems to be Solved by the Invention

Accordingly, it is an object of the present invention to provide an industrially advantageous process for producing high quality products of (3R,4S)-3-cyclopropylaminomethyl-4-fluoropyrrolidine or enantiomers thereof that are useful as intermediates for the production of various pharmaceutical products.

Means for Solving the Problems

To achieve the above-described objective, the present inventors sought a novel synthetic process of (3R,4S)-3-cyclopropylaminomethyl-4-fluoropyrrolidine or enantiomers thereof and found that (3R,4S)-3-cyclopropylcarbamoyl-4-hydroxypyrrolidine-1-carboxylic acid alkyl ester derivatives, novel intermediates derived from highly stereoselective asymmetric hydrogenation of 1-protected-4-alkoxycarbonyl-3-oxopyrrolidine, and their enantiomers exhibit good crystallinity and stability, and that the enantiomeric and diastereomeric by-products can be effectively separated from these compounds. The present inventors then found that high quality, highly pure products of (3R,4S)-3-cyclopropylaminomethyl-4-fluoropyrrolidine or enantiomers thereof can be produced in stable yields in a simple process by carrying out the synthesis via these intermediates. These findings ultimately led to the present invention.

Accordingly, the present invention comprises the following:

(1) A method for producing an optically active 3-cyclopropylaminomethyl-4-fluoropyrrolidine represented by the following chemical formula (IX):

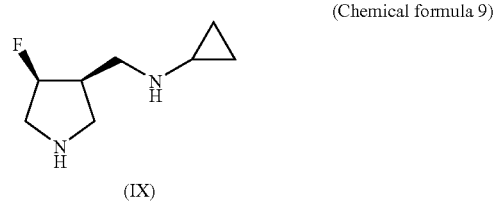

(Chemical formula 9)

(IX)

or an enantiomer thereof and/or a salt or a hydrate thereof, comprising the steps of:

asymmetrically hydrogenating, with a transitional metal catalyst, a 1-protected-4-oxo-3-pyrrolidinecarboxylic acid ester derivative represented by the following general formula (I):

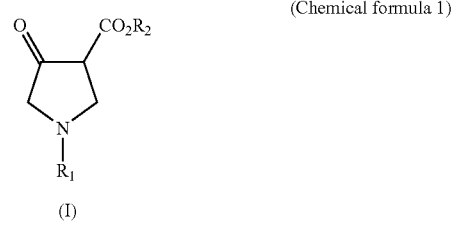

(Chemical formula 1)

(I)

(wherein $R_1$ is a protecting group for amino group; and $R_2$ is a lower alkyl group) to obtain an optically active 4-hydroxy-3-pyrrolidine carboxylic acid ester derivative of the following general formula (II):

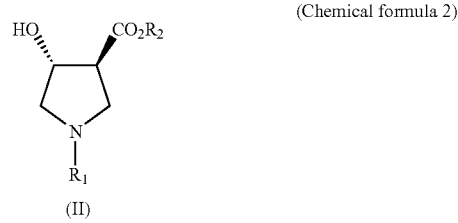

(Chemical formula 2)

(II)

(wherein $R_1$ and $R_2$ are as defined above) or an enantiomer thereof;

hydrolyzing the ester group of the compound of the general formula (II) to obtain an optically active 4-hydroxy-3-pyrrolidine carboxylic acid represented by the following general formula (III):

(Chemical formula 3)

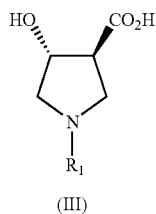

(III)

(wherein R₁ is as defined above) or an enantiomer thereof;

condensing the compound of the general formula (III) with cyclopropylamine (IV):

(Chemical formula 4)

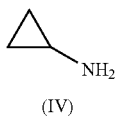

(IV)

to obtain an optically active N-cyclopropyl-4-hydroxy-3-pyrrolidine carboxylic amide derivative represented by the following general formula (V):

(Chemical formula 5)

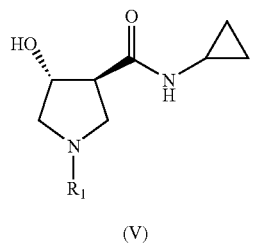

(V)

(wherein R₁ is as defined above) or an enantiomer thereof;

reducing the amide group of the compound of the general formula (V) to obtain an optically active 4-hydroxy-3-cyclopropylaminopyrrolidine derivative represented by the following general formula (VI):

(Chemical formula 6)

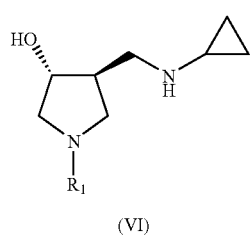

(VI)

(wherein R₁ is as defined above) or an enantiomer thereof and/or a salt or a hydrate thereof;

protecting the amino group of the compound of the general formula (VI) to obtain an optically active 4-hydroxy-3-cyclopropylamino pyrrolidine derivative represented by the following general formula (VII):

(Chemical formula 7)

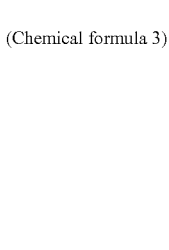

(VII)

(wherein R₁ is as defined above; and R₃ is also an protecting group for amino group and is the same definition as R₁) or an enantiomer thereof;

fluorinating the hydroxyl group at 4th position of the compound of the general formula (VII) to obtain an optically active 3-cyclopropylaminomethyl-4-fluoropyrrolidine derivative represented by the following general formula (VIII):

(Chemical formula 8)

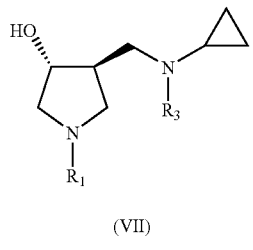

(VIII)

(wherein R₁ and R₃ are as defined above) or an enantiomer thereof; and removing the amino-protecting groups R₁ and R₃ of the compound of the general formula (VIII) to obtain the desired compound.

(2) The method for producing optically active 3-cyclopropylaminomethyl-4-fluoropyrrolidine or an enantiomer thereof and/or a salt or a hydrate thereof according to (1) above, wherein, the amino-protecting groups the R₁ and R₃ represent are each an aralkyl group, such as a benzyl group and a p-methoxybenzyl group, or an alkoxycarbonyl group, such as a methoxycarbonyl group, an ethoxycarbonyl group, a propyloxycarbonyl group, an isopropyloxycarbonyl group, a butyloxycarbonyl group, an isobutyloxycarbonyl group, a tert-butyloxycarbonyl group and an benzyloxycarbonyl group.

(3) An N-cyclopropyl-4-hydroxy-3-pyrrolidine carboxamide derivative represented by the following general formula (V):

(Chemical formula 10)

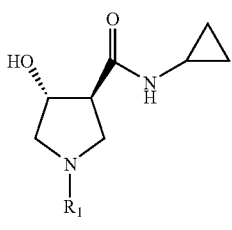

(V)

(wherein R₁ is an amino-protecting group), or an enantiomer thereof.

(4) The N-cyclopropyl-4-hydroxy-3-pyrrolidine carboxamide derivative, or an enantiomer thereof according to (3) above, wherein the amino-protecting group that $R_1$ represent is an aralkyl group, such as a benzyl group and a p-methoxybenzyl group, or an alkoxycarbonyl group, such as a methoxycarbonyl group, an ethoxycarbonyl group, a propyloxycarbonyl group, an isopropyloxycarbonyl group, a butyloxycarbonyl group, an isobutyloxycarbonyl group, a tert-butyloxycarbonyl group and an benzyloxycarbonyl group.

(5) The N-cyclopropyl-4-hydroxy-3-pyrrolidine carboxamide derivative, or an enantiomer thereof according to (3) above, wherein the compound of the general formula (V) is (3R,4S)-3-(N-cyclopropyl)carbamoyl-4-hydroxypyrrolidine-1-carboxylic acid benzyl ester, (3S,4R)-3-(N-cyclopropyl)carbamoyl-4-hydroxypyrrolidine-1-carboxylic acid benzyl ester, (3R,4S)-3-(N-cyclopropyl)carbamoyl-4-hydroxypyrrolidine-1-carboxylic acid tert-butyl ester, (3S,4R)-3-(N-cyclopropyl)carbamoyl-4-hydroxypyrrolidine-1-carboxylic acid tert-butyl ester, (3R,4S)-1-benzyl-N-cyclopropyl-4-hydroxy-3-pyrrolidine carboxamide or (3S,4R)-1-benzyl-N-cyclopropyl-4-hydroxy-3-pyrrolidine carboxamide.

EFFECT OF THE INVENTION

According to the present invention, a process has been found that uses (3R,4S)-3-cyclopropylcarbamoyl-4-hydroxypyrrolidine-1-carboxylic acid alkyl ester derivatives, novel intermediates derived from highly stereoselective asymmetric hydrogenation of 1-protected-4-alkoxycarbonyl-3-oxopyrrolidine, and their enantiomers to produce highly pure products of (3R,4S)-3-cyclopropylaminomethyl-4-fluoropyrrolidine or enantiomers thereof, or salts or hydrates thereof in high yields. The present invention thus provides an industrial process for the production of (3R,4S)-3-cyclopropylaminomethyl-4-fluoropyrrolidine or enantiomers thereof as well as salts or hydrates thereof that are useful as intermediates for the production of antimicrobial agents.

BEST MODE FOR CARRYING OUT THE INVENTION

The process according to the present invention for producing (3R,4S)-3-cyclopropylaminomethyl-4-fluoropyrrolidine, or enantiomers thereof and salts or hydrates thereof, can be summarized in the following scheme:

(Chemical formula 11)

Scheme: [0032]

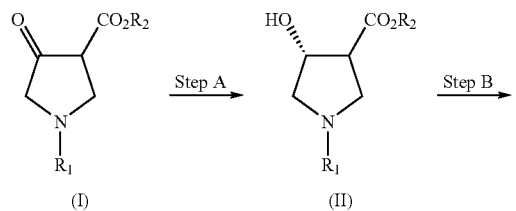

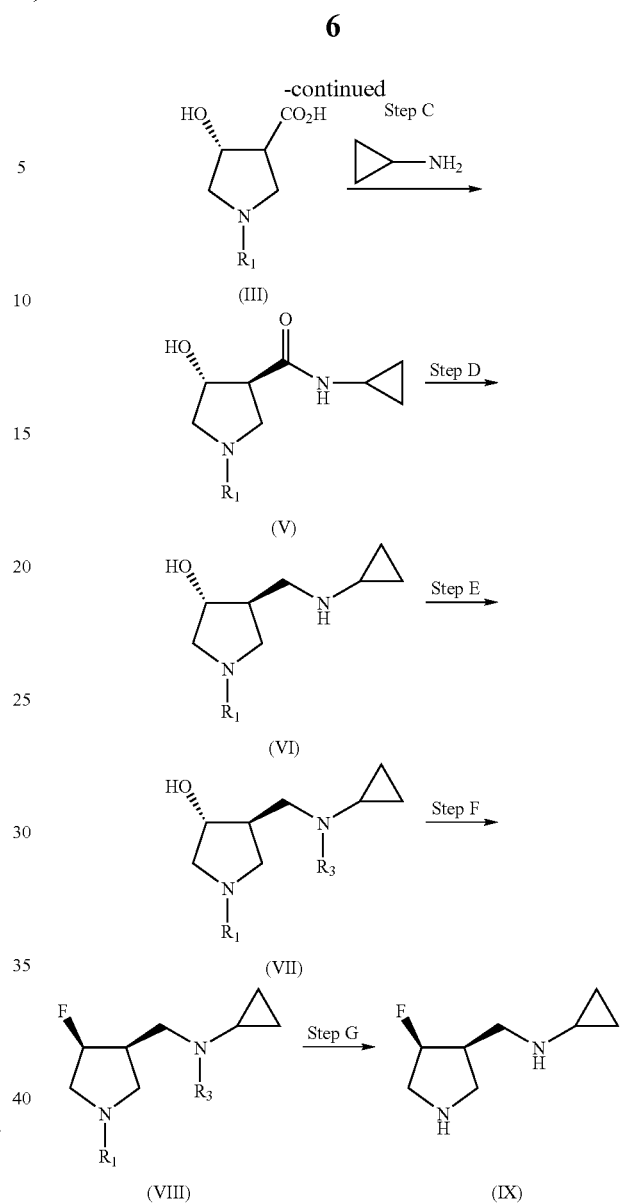

(wherein $R_1$, $R_2$ and $R_3$ are as defined above).

For ease of understanding, the structure of a compound may be given in this description by a specific structural formula that shows a particular isomer of the compound. However, the present invention encompasses all isomers, such as optical isomers based on asymmetric carbons, stereoisomers and tautomers, and mixtures of such isomers that can arise from the compound, and is not limited to the exact compounds given by the formula. The invention also encompasses all salts and hydrates of the compound.

As used herein, the term "C1-4 lower alkyl" that $R_2$ represents refers to a straight or branched alkyl group having 1 to 4 carbon atoms. Specific examples include a methyl group, an ethyl group, a n-propyl group, an i-propyl group, a n-butyl group, an i-butyl group, a sec-butyl group and a tert-butyl group.

As used herein, the amino-protecting group that $R_1$ and $R_3$ represent may be any protecting group commonly used as an amino-protecting group. Examples include aralkyl groups, such as a benzyl group and a p-methoxybenzyl group; alkoxycarbonyl groups, such as a methoxycarbonyl group, an ethoxycarbonyl group, a propyloxycarbonyl group, an isopropyloxycarbonyl group, a butyloxycarbonyl group, an isobutyloxycarbonyl group, a t-butyloxycarbonyl group and a benzyloxycarbonyl group; 1-(alkoxy)alkyl groups, such as a methoxymethyl group, a methoxyethoxymethyl group, a 1-(ethoxy)ethyl group and a methoxyisopropyl group; and acyl groups, such as an acetyl group, a trifluoroacetyl group, a propionyl group, a butyryl group, a pivaloyl group, a benzoyl group and a methylbenzoyl group. Of these protective groups, aralkyl groups and alkoxycarbonyl groups are preferred because they make the intermediates particularly handleable. Of these aralkyl groups and alkoxycarbonyl groups, a benzyl group, a benzyloxycarbonyl group and a tert-butoxycarbonyl group are particularly preferred.

Each step of the production process of the present invention will now be described in detail.

The starting material used in the process of the present invention is a 1-protected-4-oxo-3-pyrrolidine carboxylic acid ester derivative represented by the general formula (I). The compound of the general formula (I) can be prepared according to the technique reported by Choi and Dong Rack et al (Bioorganic & Medicinal Chemistry Letter (2004), 14(5), 1273-1277). For example, 1-benzyloxycarbonyl-4-ethoxycarbonyl-3-oxopyrrolidine can be produced in the following manner: a Michael addition is performed using glycine ethyl ester hydrochloride and ethyl acrylate. Using reagents such as benzyl chloroformate, the resulting secondary amino group is protected with a benzyloxycarbonyl group. A base such as sodium ethoxide is then used to cause the protected product to undergo the intramolecular ring-forming reaction to form the desired product. Other derivatives can be produced in a similar manner.

(Step A)

In this step, asymmetric hydrogenation is carried out. The asymmetric hydrogenation reaction can be carried out by using a hydrogen source in the presence of an optically active catalyst. The optically active catalyst used is a transitional metal complex having a chiral ligand. The transitional metal may be ruthenium, rhodium, iridium, nickel, palladium and platinum. Ruthenium is preferred due to its availability. While the chiral ligand may be any of the commonly used chiral ligands, those described in the following journal article may preferably be used: CATALYTIC ASYMMETRIC SYNTHESIS Second Edition, 2000, WILEY-VCH, p 2-6.

Examples of such chiral ligands include C2-chiral diphosphines and enantiomers thereof, such as (S,S)-BDPP, (R,R)-BICP, (R)-BIMOP, (S)-BINAP, (S)-TolBINAP, (S)-XylBINAP, (S)-DTBBINAP, (S)-p-MeO-BINAP, (S)-BINAP-SO$_3$Na, (S)-Cy-BINAP, (S)-BIPHEMP, (S)-MeO-BIPHEP, (S)-p-Tol-MeO-BIPHEP, di-t-Bu-MeO-BIPHEP, (S)-Fr-MeO-BIPHEP, (S)-BICPEP, (S)-BICHEP, (R,R)-BIPNOR, (R,R)-Bis P, (S,S)-t-BuBis P*, (S)-bis-steroidal phosphine, (S)-tetraMe-BITIANP, (S)-Me-BPE, (S)-Et-BPE, (S)-1-BPE, (S,S)-CHIRAPHOS, (R,R)-CDP, (S,S)-DIOP, (S,S)-DIOP-OH, (S,S)-MOD-DIOP, (S,S)-CyDIOP, (S,S)-DIPAMP, (S,S)-Me-DuPHOS, (S,S)-Et-DuPHOS, (S,S)-i-Pr-DuPHOS, (S,S)-FerroPHOS, (S)-HB-BINAP, (S,S)-NORPHOS, (R,S,R,S)-Me-PennPhos, (S)-[2.2]PHANEPHOS, (S,S)-PYRPHOS, (S,S)-RENORPHOS, (S,S,S,S)-RoPHOS, (R,R)-TBPC, (R,R)-(S,S)-TRAP, (R,R)-(S,S)-EtTRAP, (R,R)-(S,S)-i-BuTRAP and (S)-SEGPHOS; non-C2-chiral diphosphines and enantiomers thereof, such as (R)—(S)-BPPFA, (R)-(S)-BPPFOH, (2S,4S)-BPPM, (R)-(S)-BCPM, (R)-(S)-MCCPM, (R)-(S)-m-CH3POPPM, (R)-(S)-MOD-BCPM, (S)-CAMP, (R)-cy$_2$-BIPHEMP, (S,R,R,R)-TMO-DEGUPHOS, (R)-(S)-JOSIPHOS, (R)-(S)-XYLIPHOS, (R)-(S)-xyl$_2$ PF-Pxyl$_2$, (R)-(S)-MOD-XYLIPHOS, (R)-MOC-BIMOP, (1R,2R)-PPCP, (R)-PROPHOS, (R)-BENZPHOS, (R)-CyCPHOS and (S,S)-SulfBDPP; bisphosphonites and enantiomers thereof, such as (S,S)-BDPCH, (S,S)-BDPCP, (S,R)-BICPO, Ph-β-GLUP, Ph-β-GLUP-OH and (R,R,R)-spirOP; and amidophosphines, aminophosphines and enantiomers thereof, such as (R)-BD-PAB, (1S,2R)-DPAMPP, (R)-H$_8$-BDPAB, (S)-Cp, Cp-IndoNOP, (S,2S)-Cr(CO)$_3$-Cp, Cp-IndoNOP, (S)-isoAlaNOP, (S)-Ph, Cp-isoAlaNOP, (S)-Cp, Cp-isoAlaNOP, (S)-Ph, Cp-methyllactamide, (S)-Ph,Ph-oxoProNOP, (S)-Cp, Cp-oxoProNOP, (S)-Cy, Cy-oxoProNOP, (R)-PINDOPHOS, (S,S)-PNNP and (S)-PROLOPHOS. (S)-BINAP is preferably used due to its availability.

When the transitional metal complexes are used as catalysts, 0.001 to 1.0 mols of the catalyst are used for 1 mol of the reaction substrate.

The hydrogen source may be hydrogen and formic acid/triethylamine system, formic acid/α-phenethylamine system, formic acid/triphenylamine system or 2-propanol.

The reaction generally requires a solvent. Examples of the solvent include water; organic acids, such as formic acid and acetic acid; esters, such as ethyl acetate and butyl acetate; aromatic compounds, such as benzene, toluene and xylene; hydrocarbons, such as hexane, heptane and cyclohexane; alcohols, such as methanol, ethanol, t-butyl alcohol, ethylene glycol and diethylene glycol; ethers, such as dioxane, tetrahydrofuran, dimethoxyethane and diglyme; halogenated hydrocarbons, such as dichloromethane, chloroform, carbon tetrachloride and 1,2-dichloroethane; and mixtures thereof. Of these, alcohols such as ethanol and halogenated hydrocarbons such as dichloromethane are preferred.

The reaction is typically carried out at a temperature in the range of −20° C. to 200° C., and preferably in the range of 25° C. to 100° C.

The reaction pressure is typically in the range of atmospheric pressure to 20 MPa.

(Step B)

In this step, the ester group is hydrolyzed. The ester hydrolysis can be performed using conditions commonly used for this purpose. For example, the reaction can be carried out in the presence of an alkali reagent, such as sodium hydroxide, or in the presence of an inorganic acid, such as hydrochloric acid, or an organic acid, such as trifluoro acetic acid, and in a solvent, such as an alcohol (such as methanol, ethanol and propanol), tetrahydrofuran, t-butyl methyl ether and cyclopentyl methyl ether. While the reaction may be carried out at any temperature in the range of −20° C. to the boiling point of the solvent used, it is preferably carried out in the range of 0° C. to room temperature.

(Step C)

In this step, the pyrrolidine carboxylic acid derivative (III) is amidated with cyclopropylamine. The amidation reaction can be performed by using commonly used condensation conditions.

When a condensation agent is used, it may be any condensation agent that can form an amide linkage between a carboxylic acid and an amine. The condensation agent is preferably 1-ethyl-3-(3-dimethylaminopropyl)carbodiimide hydrochloride, dicyclohexylcarbodiimide, diethyl phosphorocyanidate, carbodiimidazole, diphenylphosphoryl azide or 1-hydroxybenzotriazole. Of these, 1-ethyl-3-(3-dimethylaminopropyl)carbodiimide hydrochloride and 1-hydroxybenzotriazole are particularly preferred. The base used may be any base that does not interfere with the reaction. Examples include organic amines such as triethylamine, trimethylamine, pyridine, dimethylaniline, N-methylmorpholine and 4-dimethylaminopyridine. Of these, triethylamine is particularly preferred. The reaction generally requires a solvent, examples including esters, such as ethyl acetate and butyl acetate; aromatic compounds, such as benzene, toluene and xylene; hydrocarbons, such as hexane, heptane and cyclohexane; ethers, such as dioxane, tetrahydrofuran, dimethoxyethane and diglyme; halogenated hydrocarbons, such as dichloromethane, chloroform, carbon tetrachloride and 1,2-dichloroethane; nitriles, such as acetonitrile; and mixtures thereof. Of these, tetrahydrofuran, ethyl acetate and acetonitrile are particularly preferred in the reaction.

While the reaction may be carried out at any temperature in the range of −20° C. to the boiling point of the solvent used, it is preferably carried out at a temperature in the range of 0° C. to the boiling point of the solvent used.

Alternatively, the compound (III) may be reacted with a reactive derivative to form the compound (IV). Examples of such reactive derivatives include acid halides, such as acid chlorides and acid bromides; active esters, such as N-hydroxybenzotriazole and N-hydroxysuccinimide; mixed anhydrides with monoethyl carbonate and monophenyl carbonate; and anhydrides of the compound (III). Active esters using N-hydroxybenzotriazole are particularly preferred. The reaction is typically carried out either in the absence of solvents or in the presence of an inert solvent. When necessary, a base is added to the reaction system. The base may be any base that does not interfere with the reaction. Examples of the base include organic amines, such as triethylamine, trimethylamine, pyridine, dimethylaniline, N-methylmorpholine and 4-dimethylaminopyridine. Of these, triethylamine is preferred. Examples of the solvent include esters, such as ethyl acetate and butyl acetate; aromatic compounds, such as benzene, toluene and xylene; hydrocarbons, such as hexane, heptane and cyclohexane; ethers, such as dioxane, tetrahydrofuran, dimethoxyethane and diglyme; halogenated hydrocarbons, such as dichloromethane, chloroform, carbon tetrachloride and 1,2-dichloroethane; nitriles, such as acetonitrile; and mixtures thereof. Of these, tetrahydrofuran, ethyl acetate and acetonitrile are particularly preferred in the reaction. While the reaction may be carried out at any temperature in the range of −20° C. to the boiling point of the solvent used, it is preferably carried out at a temperature in the range of 0° C. to the boiling point of the solvent used.

(Step D)

In this step, the amide group is reduced. Examples of the reducing agent used include $BH_3$-THF, $BH_3$—$SMe_2$, LiAlH(OMe)$_3$, LiAlH$_4$, AlH$_3$, LiBEt$_3$H, (i-Bu)$_2$AlH, NaAlEt$_2$H$_2$, NaBH$_4$—ZnCl$_2$, NaBH$_4$—BF$_3$OEt$_2$, NaBH$_4$-TMSCl, NaBH$_4$—LiCl, NaBH$_4$—AlCl$_3$ and NaBH$_4$—CoCl$_2$. Of these, $BH_3$-THF is preferred.

The reaction generally requires a solvent. Examples of the solvent include ethers, such as tetrahydrofuran, cyclopentyl methyl ether, dioxane, dimethoxyethane and diglyme; aromatic compounds, such as benzene, toluene and xylene; hydrocarbons, such as hexane, heptane and cyclohexane; alcohols, such as methanol, ethanol, t-butyl alcohol, ethylene glycol and diethylene glycol; and mixtures thereof.

While the reaction may be carried out at any temperature in the range of −70° C. to the boiling point of the solvent used, it is preferably carried out at a temperature in the range of −10° C. to the boiling point of the solvent used. When $BH_3$-THF is used as the reducing agent, typically 1.0 to 20 mols, preferably 1.0 to 3.0 mols of the reducing agent are used for 1 mol of the compound (IV). The reaction generally requires a solvent, examples including ethers, such as tetrahydrofuran, cyclopentyl methyl ether, dioxane, dimethoxyethane and diglyme; aromatic compounds, such as benzene, toluene and xylene; hydrocarbons, such as hexane, heptane and cyclohexane; and mixtures thereof. Of these solvents, ethers are preferred with tetrahydrofuran being particularly preferred. While the reaction may be carried out at any temperature in the range of −70° C. to the boiling point of the solvent used, it is preferably carried out at a temperature in the range of −10° C. to the boiling point of the solvent used.

(Step E)

In this step, the protecting group $R_3$ is introduced into the amino group. The amino-protecting group that $R_3$ represents may be any protecting group commonly used as an amino-protecting group. Examples include aralkyl groups, such as a benzyl group and a p-methoxybenzyl group; alkoxycarbonyl groups, such as a methoxycarbonyl group, an ethoxycarbonyl group, a propyloxycarbonyl group, an isopropyloxycarbonyl group, a butyloxycarbonyl group, an isobutyloxycarbonyl group, a t-butyloxycarbonyl group and a benzyloxycarbonyl group; 1-(alkoxy)alkyl groups, such as a methoxymethyl group, a methoxyethoxymethyl group, a 1-(ethoxy)ethyl group and a methoxyisopropyl group; and acyl groups, such as an acetyl group, a trifluoroacetyl group, a propionyl group, a butyryl group, a pivaloyl group, a benzoyl group and a methylbenzoyl group. Of these protecting groups, aralkyl groups and alkoxycarbonyl groups are preferred because they make the intermediates particularly handleable. Of these aralkyl groups and alkoxycarbonyl groups, a benzyl group, a benzyloxycarbonyl group and a tert-butoxycarbonyl group are particularly preferred. These protecting groups can be introduced by using any of the described techniques (See, for example, Green, T. W.; Wuts, P. G. M. "Protective Groups in Organic Synthesis," 2nd Ed., Wiley Interscience Publication, John-Wiley & Sons, New York, 1991, p 309-p 348).

For example, when the amino-protecting group is a benzyl group, an aralkyl-containing compound such as benzyl bromide and benzyl chloride may be used in a proper solvent in the presence of a base. When the amino-protecting group is an alkoxycarbonyl group such as t-butoxycarbonyl group and benzyloxycarbonyl group, a chlorocarbonate ester such as benzyl chlorocarbonate, or a dicarbonate diester such as t-butoxycarbonyl dicarbonate may be used. A base is used when necessary. Examples of the base include inorganic bases, such as lithium hydroxide, sodium hydroxide, potassium hydroxide, sodium carbonate, potassium carbonate, cesium carbonate, sodium bicarbonate and potassium bicarbonate; organic bases, such as triethylamine, diisopropylethylamine, 4-methylmorpholine, 4-ethylmorpholine, pyridine, 1-methylimidazole, 1,2-dimethylimidazole, 1,5-diazabicyclo[4.3.0]-5-nonene and 1,5-diazabicyclo[5.4.0]-5-undecene; and alkali metal alkoxides, such as lithium methoxide, lithium ethoxide, sodium methoxide, sodium ethoxide, sodium t-butoxide, potassium methoxide, potassium ethoxide and potassium t-butoxide.

The reaction generally requires a solvent. Examples of the solvent include ethers, such as tetrahydrofuran, cyclopentylmethyl ether, dioxane, dimethoxyethane and diglyme; aromatic compounds, such as benzene, toluene and xylene; hydrocarbons, such as hexane, heptane and cyclohexane; alcohols, such as methanol, ethanol, t-butyl alcohol, ethylene glycol and diethylene glycol; water; and mixtures thereof.

While the reaction may be carried out at any temperature in the range of −70° C. to the boiling point of the solvent used, it is preferably carried out in the range of −10° C. to the boiling point of the solvent used.

(Step F)

In this step, the hydroxyl group is converted into the fluorine group. The fluorination reaction can be carried out by using commonly used conditions. For example, a perfluoroalkylsulfonyl fluoride, such as perfluoro-1-butanesulfonyl fluoride or 1-octanesulfonyl fluoride or a dialkylaminosulfur trifluoride such as diethylaminosulfur trifluoride, morpholinosulfur trifluoride or bis(2-methoxyethyl)aminosulfur trifluoride is used for the purpose in a proper solvent and when necessary, in the presence of a base.

Perfluoroalkylsulfonyl fluorides are generally used in conjunction with a base, which may be any base that does not interfere with the reaction. Examples of the base include organic amines, such as 1,8-diazabicyclo[5.4.0]undeca-7-ene, triethylamine, trimethylamine, pyridine, dimethylaniline and N-methylmorpholine. Of these bases, 1,8-diazabicyclo[5.4.0]undeca-7-ene is particularly preferred.

The reaction generally requires a solvent. Examples of the solvent include esters, such as ethyl acetate and butyl acetate; aromatic compounds, such as benzene, toluene and xylene; hydrocarbons, such as hexane, heptane and cyclohexane; ethers, such as dioxane, tetrahydrofuran, dimethoxyethane and diglyme; halogenated hydrocarbons, such as dichloromethane, chloroform, carbon tetrachloride and 1,2-dichloroethane; nitriles, such as acetonitrile; and mixtures thereof. Of these solvents, toluene is particularly preferred. While the reaction may be carried out at any temperature in the range of −70° C. to the boiling point of the solvent used, it is preferably carried out in the range of −10° C. to the boiling point of the solvent used.

When dialkylaminosulfur trifluorides are used, a solvent is generally required. Examples of the solvent include esters, such as ethyl acetate and butyl acetate; aromatic compounds, such as benzene, toluene and xylene; hydrocarbons, such as hexane, heptane and cyclohexane; ethers, such as dioxane, tetrahydrofuran, dimethoxyethane and diglyme; halogenated hydrocarbons, such as dichloromethane, chloroform, carbon tetrachloride and 1,2-dichloroethane; nitriles, such as acetonitrile; and mixtures thereof. Of these solvents, dichloromethane and acetonitrile are particularly preferred. While the reaction may be carried out at any temperature in the range of −70° C. to the boiling point of the solvent used, it is preferably carried out in the range of −10° C. to the boiling point of the solvent used.

(Step G)

In this step, the amino-protecting group is removed. The introduction and the removal of these protecting groups can be performed by using any of the described techniques (Green, T. W.; Wuts, P. G. M. "Protective Groups in Organic Synthesis," 2nd Ed., Wiley Interscience Publication, John-Wiley & Sons, New York, 1991, p 309-p 348). For example, when $R_1$ and $R_3$ of the compound of the general formula (VII) are each an aralkyloxy group, such as benzyloxycarbonyl group, or an aralkyl group, such as benzyl group and p-methoxybenzyl group, the protecting groups can be removed at once by carrying out catalytic hydrogenation in the presence of a catalyst. When $R_1$ and $R_3$ of the compound (VII) are each a t-butoxycarbonyl group, the protecting groups can be removed at once by the use of an organic acid or an inorganic acid.

When $R_1$ and $R_3$ of the compound (VII) require different conditions for removal, the above-described techniques may be combined. Aralkyl groups such as benzyloxycarbonyl group and benzyl group can be removed by performing catalytic hydrogenation in the presence of a hydrogen source. Examples of the catalyst that can be used include palladium catalysts, such as palladium/carbon, palladium/alumina, palladium black and palladium oxide. Of these, palladium/carbon is particularly preferred.

The hydrogen source may be hydrogen and formic acid/triethylamine system, formic acid/α-phenethylamine system, formic acid/triphenylamine system or 2-propanol. Of these, hydrogen is particularly preferred. The reaction pressure is typically in the range of atmospheric pressure to 10 MPa, and preferably in the range of atmospheric pressure to 1 MPa.

The reaction generally requires a solvent. Examples of the solvent include alcohols, such as methanol, ethanol, t-butyl alcohol, ethylene glycol and diethylene glycol; water; ethers, such as tetrahydrofuran, cyclopentyl methyl ether, dioxane, dimethoxyethane and diglyme; aromatic compounds, such as benzene, toluene and xylene; hydrocarbons, such as hexane, heptane and cyclohexane; and mixtures thereof.

While the reaction may be carried out at any temperature in the range of 0° C. to the boiling point of the solvent used, it is preferably carried out in the range of room temperature to the boiling point of the solvent used. To accelerate the reaction, an acid, such as sulfuric acid, hydrochloric acid, phosphoric acid and perchloric acid, or a base, such as ammonia, pyridine, triethylamine, sodium hydroxide and potassium hydroxide, may be added to the reaction system.

Any solvent that is commonly used in organic synthesis and does not interfere with the reaction may be used in the present invention. Examples of such solvents include lower alcohols, such as methanol, ethanol, propanol and butanol; polyalcohols, such as ethylene glycol and glycerol; ketones, such as acetone, methyl ethyl ketone and cyclohexane; ethers, such as diethyl ether, diisopropyl ether, tetrahydrofuran, dioxane, 2-methoxyethanol, 1,2-dimethoxyethane and cyclopentyl methyl ether; nitriles, such as acetonitrile and propionitrile; esters, such as methyl acetate, ethyl acetate, isopropyl acetate and butyl acetate; halogenated hydrocarbons, such as dichloromethane, chloroform, carbon tetrachloride and 1,2-dichloroethane; aromatic compounds, such as benzene, toluene, xylene, monochlorobenzene, nitrobenzene, pyridine, quinoline, collidine and phenol; hydrocarbons, such as pentane, cyclohexane, hexane, heptane, petroleum ether and petroleum benzene; amines, such as ethanolamine, diethylamine, triethylamine, pyrrolidine, piperazine, morpholine, aniline, dimethylaniline, benzylamine and toluidine; amides, such as formamide, N-methylpyrrolidone and N,N-dimethylformamide; sulfoxides, such as dimethyl sulfoxide and sulfolane; hexamethylphosphoric triamide; water; and other commonly used solvents and mixtures of two or more of these solvents, which may contain each solvent in any proportion. When desired, it may be purified and isolated upon completion of the reaction by using common separation techniques (such as extraction, recrystallization and chromatography).

The compounds of the present invention can be produced by the processes described in examples hereinbelow. However, these examples are intended to be only illustrative and the compounds of the present invention are by no means limited to those presented in the examples.

EXAMPLES

Reference Example 1

Synthesis of ethyl 3-(ethoxycarbonylmethylamino)propionate (Chemical formula 12)

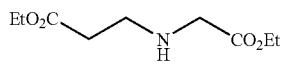

150 g of glycine ethyl ester hydrochloride (1.07 mol) was mixed with 1.200 L of ethanol. To this mixture, 110 mL of ethyl acrylate (1.02 mol) was added at an internal temperature of 2 to 25° C. 150 mL of triethylamine (1.08 mol) was then added dropwise at an internal temperature of 20 to 21° C. over 5 minutes. Subsequently, the mixture was stirred at an internal temperature of 23 to 27° C. for 8.5 hours and was allowed to stand overnight. The insoluble material was separated by filtration and the filtrate was evaporated under reduced pressure. 300 mL of ethyl acetate was added to the resulting residue and the insoluble material was separated by filtration and washed with 50 mL of ethyl acetate. The filtrate and the wash were combined and concentrated under reduced pressure. The resulting residue was distilled under reduced pressure (533 Pa, 130° C.) to give 138 g of the title compound as a colorless oil (67% yield).

$^1$H-NMR (CDCl$_3$, 400 MHz) δ: 1.27 (3H, t, J=7.1 Hz), 1.28 (3H, t, J=7.3 Hz), 2.51 (2H, t, J=6.6 Hz), 2.90 (2H, t, J=6.6 Hz), 3.42 (2H, s), 4.15 (2H, q, J=7.1 Hz), 4.19 (2H, q, J=7.1 Hz).

FAB-MS (positive): 204 [M+H]$^+$

Reference Example 2

Synthesis of ethyl 3-benzyloxycarbonyl-3-(ethoxycarbonylmethylamino)propionate

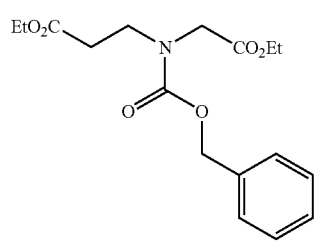

(Chemical formula 13)

0.95 kg of ethyl 3-(ethoxycarbonylmethylamino)propionate (4.68 mol) was dissolved in 2.85 L of ethanol and 2.85 L of water. To this solution, 0.41 kg of sodium bicarbonate (4.91 mol) was added under stirring. Subsequently, 0.84 kg of benzylchloroformate (4.91 mol) was added dropwise at an internal temperature of 28 to 35° C. and the mixture was stirred at an internal temperature of 28 to 35° C. for 2 hours. Ethanol was evaporated under reduced pressure and 9.51 L of ethyl acetate was added. The mixture was then stirred for 5 minutes. The mixture was allowed to stand and the organic layer (top layer) was collected. To this layer, 4.8 L of water was added and the mixture was stirred for 5 minutes. The mixture was allowed to stand again and the organic layer (top layer) was collected. To this layer, 4.8 L of 28% brine was added and the mixture was stirred for 5 minutes. The mixture was allowed to stand again and the organic layer (top layer) was collected. To this layer, 0.57 kg of anhydrous sodium sulfate was added and the mixture was stirred for 1 hour. The solid was separated by filtration and washed with 0.95 L of ethyl acetate. The filtrate and the wash were combined and concentrated under reduced pressure. The resulting product was dried under reduced pressure at an external temperature of 50° C. for 30 minutes. This gave 1.64 kg of a crude product of the title compound as a colorless oil. This product was used in the subsequent step without further purification.

ESI-MS (positive): m/z 338 [M+H]$^+$

Reference Example 3

Synthesis of 1-benzyl 3-ethyl 4-oxopyrrolidine-1,3-dicarboxylate

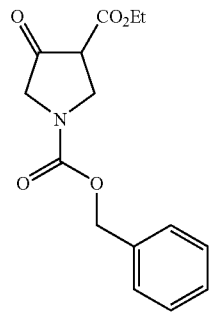

(Chemical formula 14)

0.35 kg of sodium ethoxide (5.15 mol) was suspended in 9.47 L of tetrahydrofuran. While this suspension was stirred, 3.16 L of a tetrahydrofuran solution containing 1.64 kg of the crude product of ethyl 3-benzyloxycarbonyl-3-(ethoxycarbonylmethylamino)propionate (equivalent to 4.68 mol) was added dropwise at an internal temperature of 25 to 32° C. The mixture was then stirred at an internal temperature of 25 to 32° C. for 2 hours. While the reaction mixture was stirred, 5.15 L of 1 mol/L hydrochloric acid (pH 4.78) was added at an internal temperature of 27 to 28° C. and the mixture was stirred for 10 minutes (pH changed from 4.78 to 4.76). Subsequently, tetrahydrofuran (approx. 12 L) was evaporated under reduced pressure. To the resulting residue, 7.89 L of ethyl acetate was added and the mixture was stirred for 5 minutes. The reaction mixture was then allowed to stand and the organic layer (top layer) was collected. To this layer, 3.95 L of water was added and the mixture was stirred for 5 minutes. The mixture was allowed to stand again and the organic layer (top layer) was collected. To this layer, 3.95 L of 28% brine was added and the mixture was stirred for 5 minutes. The mixture was allowed to stand again and the organic layer (top layer) was collected. To this layer, 0.39 kg of anhydrous sodium sulfate was added and the mixture was stirred for 1 hour. The resulting solid was separated by filtration and washed with 1.58 L of ethyl acetate. The filtrate and the wash were combined and concentrated under reduced pressure. This product was then dried under reduced pressure at an external temperature of 40° C. for 30 minutes. The resulting pale brown oil (1.52 kg) was dissolved in 9.47 L of diisopropyl ether and the solution was stirred at an internal temperature of 25° C. Once the formation of crystals was observed (internal temperature of 25° C.), the solution was further stirred for 15 minutes at an internal temperature of 25 to 28° C. Subsequently, the solution was cooled in an ice bath under stirring and was kept stirred for 30 minutes at an internal temperature of 10° C. or below. The crystals were then collected by filtration at an internal temperature of 7° C. and washed with a chilled, 4:1 mixture of diisopropylether/hexane (3.95 L, internal temperature of 3° C.). The washed crystals were drained for 15 minutes and air-dried overnight. Subsequently, the product was dried under reduced pressure at 40° C. for 9 hours. This gave 1.03 kg of the title compound as a faintly yellowish white powder (75% yield in the two steps).

Melting Point: 56.6-59.7° C.

EI-MS: m/z 91 (base peak), 291 (M)$^+$

Example 1

Synthesis of 1-benzyl 3-ethyl (3S,4R)-4-hydroxypyrrolidine-1,3-dicarboxylate

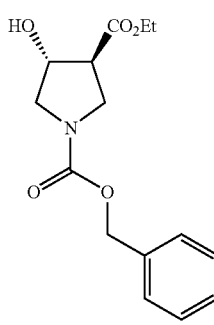

(Chemical formula 15)

90 mL of dehydrated N,N-dimethylformamide was added to 2.58 g of benzene ruthenium (II) chloride dimer (5.15 mmol) and 6.73 g of (S)-(–)-2,2,'-bis(diphenylphosphino)-1,1-binaphthyl (S-BINAP) (10.8 mmol). The mixture was stirred for 10 minutes in an oil bath at an external temperature of 97 to 102° C. in an argon atmosphere. Subsequently, the mixture was stood to be cooled at room temperature. Volatile materials were evaporated under reduced pressure in an oil bath at an external temperature of 50 to 60° C. to give a catalyst. 300 g of 1-benzyl 3-ethyl 4-oxopyrrolidine-1,3-dicarboxylate (1.03 mol) and 500 mL of dehydrated dichloromethane were placed in an autoclave and the ruthenium catalyst dissolved in 850 mL of dehydrated dichloromethane was added. The mixture was stirred for 6 hours under a hydrogen pressure of 5 MPa at an external temperature of 50 to 62° C. Hydrogen was released and the reaction mixture was concentrated under reduced pressure. This gave 320 g of the title compound as a green oil. This product was used in the subsequent step without further purification.

$^1$H-NMR (CDCl$_3$, 400 MHz) δ: 1.27 (3H, t, J=7.1 Hz), 2.31-2.40 (1H, m), 2.96-3.10 (1H, m), 3.36 (1H, ddd, J=12.0, 5.4, 2.7 Hz), 3.66 (1H, dd, J-11.2, 7.1 Hz), 3.76-3.87 (2H, m), 4.19 (2H, q, J=7.1 Hz), 4.56-4.59 (1H, m), 5.14 (2H, s), 7.29-7.37 (5H, m).

CI-MS (positive): m/z 294 [M+H]$^+$

Example 2

Synthesis of (3S,4R)-1-benzyloxycarbonyl-4-hydroxypyrrolidine-3-carboxylic acid

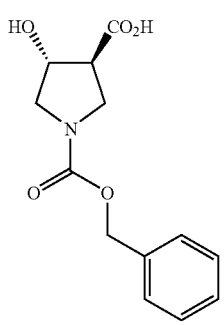

(Chemical formula 16)

639 g of 1-benzyl 3-ethyl (3S,4R)-4-hydroxypyrrolidine-1,3-dicarboxylate (equivalent to 1.03 mol) was dissolved in 3.02 L of ethanol and 3.02 L of water was added to the solution. While the mixture was stirred and cooled in an ice bath, a sodium hydroxide solution (formed by dissolving 124 g of sodium hydroxide (3.09 mol) in 3.02 L of water) was added dropwise at an internal temperature of 6.0 to 9.8° C. and the mixture was subsequently stirred at an internal temperature of 6 to 10° C. for 1 hour. This was followed by addition of 60.4 g of active carbon. The mixture was then taken out of the ice bath and stirred at room temperature for 30 minutes. The insoluble material was separated by filtration and washed with 1.21 L of water. The filtrate and the wash were combined and concentrated under reduced pressure. To the resulting residue, 3.02 L of diisopropyl ether was added and the mixture was stirred for 5 minutes. Subsequently, the mixture was allowed to standard the aqueous layer (bottom layer) was collected. To the aqueous layer, 3.02 L of diisopropyl ether was added and the mixture was stirred for 5 minutes. The mixture was allowed to stand again and the aqueous layer (bottom layer) was collected. While the aqueous layer was stirred, 0.54 L of 6 mol/L hydrochloric acid was added dropwise (pH changed from 12.8 to 1.5). To the resulting mixture, 4.83 L of ethyl acetate and 1.21 kg of sodium chloride were added and the mixture was stirred for 5 minutes. The mixture was then allowed to stand and the organic layer (top layer) was collected. To the organic layer, 3.02 L of 28% brine was added and the mixture was stirred for 5 minutes. The mixture was then allowed to stand again and the organic layer (top layer) was collected. To the organic layer, 302 g of anhydrous sodium sulfate was added and the mixture was stirred for 1 hour. The resulting solid was separated by filtration and washed with 0.90 L of ethyl acetate. The filtrate and the wash were combined and concentrated under reduced pressure to give 620 g of a crude product of the title compound as a pale brown solid. This product was used in the subsequent step without further purification.

$^1$H-NMR (CDCl$_3$, 400 MHz) δ: 3.01-3.10 (1H, m), 3.34-3.41 (1H, m), 3.54-3.86 (3H, m), 4.60 (1H, q, J=5.5 Hz), 5.13 (2H, s), 7.30-7.36 (5H, m).

CI-MS (positive): m/z 266 [M+H]$^+$

Example 3

Synthesis of benzyl (3S,4R)-3-(N-cyclopropyl)carbamoyl-4-hydroxypyrrolidine-1-carboxylate

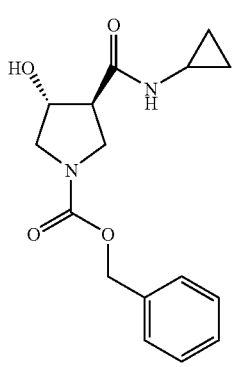

(Chemical formula 17)

5.46 L of tetrahydrofuran was added to 619 g of (3S,4R)-1-benzyloxycarbonyl-4-hydroxypyrrolidine-3-carboxylic acid (equivalent to 2.06 mol) to dissolve the compound. While this solution was stirred, 379 g of 1-hydroxybenzotriazole hydrate (2.47 mol), 294 g of cyclopropylamine (5.15 mol) and 474 g of 1-ethyl-3-(3-dimethylaminopropyl)carbodiimide hydrochloride (2.47 mol) were successively added. The resulting mixture was stirred at an internal temperature of 26 to 40° C. for 5 hours. The reaction mixture was then concentrated under reduced pressure. To the resulting residue, 2.73 L of ethyl acetate and 5.46 L of 1 mol/L hydrochloric acid were added and the mixture was stirred for 30 minutes. The precipitated solid was separated by filtration and washed with 0.55 L of ethyl acetate. The filtrate and the wash were combined, followed by addition of 2.18 L of ethyl acetate and 546 g of sodium chloride and stirring for 5 minutes. Subsequently, the mixture was allowed to stand and the organic layer (top layer) was collected. To the organic layer, 2.73 L of 10% sodium bicarbonate was added and the mixture was stirred for 5 minutes. The mixture was allowed to stand again and the organic layer (top layer) was collected. To the organic layer, 2.73 L of 28% brine was added and the mixture was stirred for 5 minutes. The mixture was then allowed to stand again and the organic layer (top layer) was collected. To the organic layer, 0.82 kg of anhydrous sodium sulfate was added and the mixture was stirred for 1 hour. The resulting solid was separated by filtration and washed with 1.09 L of ethyl acetate. The filtrate and the wash were combined and concentrated under reduced pressure to give a faint yellow solid (706 g). To this solid, 3.28 L of diisopropyl ether was added and the mixture was stirred for 30 minutes. The solid was collected by filtration and washed with 0.82 L of diisopropyl ether. The washed product was drained for 1 hour and dried by air-blowing at 50° C. for 16 hours. This gave faintly yellow white powder crystals (534 g). To 534 g of the crystals, 6.40 L of ethyl acetate was added and the mixture was heated under stirring until the crystals dissolved (internal temperature of 70° C.) The mixture was allowed to cool under stirring. Following the formation of crystals (internal temperature of 57° C.), the mixture was kept stirred until its internal temperature was 50° C. Subsequently, the mixture was cooled in a water bath while being stirred and the crystals were collected by filtration at an internal temperature of 25° C. and washed with 1.07 L of diisopropyl ether. The product was drained for 1 hour and dried by air-blowing at 60° C. for 19 hours to give 375 g of the title compound as fluffy white crystals (60% yield in the 3 steps).

Melting point: 134.5-135.2° C. $^1$H-NMR (CDCl$_3$, 400 MHz) δ: 0.44 (2H, m), 0.71-0.81 (2H, m), 2.66-2.79 (2H, m), 3.25 (1H, dd, J=10.9, 6.9 Hz), 3.37-3.62 (2H, m), 3.70-3.86 (2H, m), 4.38-4.51 (1H, m), 5.12 (2H, s), 6.29 (1H, br s), 7.28-7.38 (5H, m).

CI-MS (positive): m/z 305 [M+H]$^+$ $[\alpha]_D^{24}$ 25.0 (c=0.30, methanol)

Optical purity: 99.9% ee (HPLC Conditions)

Column =CHIRAL CELL AD-RH (4.6φ×150 mm), Daicel; precolumn =INERTSIL ODS-3 (4.0φ×10 mm), GL Sciences; detection wavelength=210 mm; flow rate=1.0 mL/min; mobile phase=diluted phosphoric acid (1 to 1000 fold); acetonitrile=75:25; RT=14.05 min.

Example 4

Synthesis of Benzyl (3S,4R)-3-cyclopropylaminomethyl-4-hydroxypyrrolidine-1-carboxylate

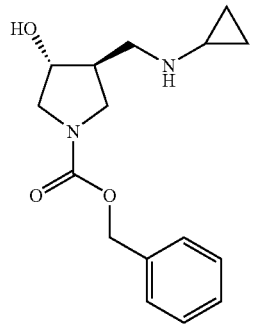

(Chemical formula 18)

364 g of benzyl (3S,4R)-3-(N-cyclopropyl)carbamoyl-4-hydroxypyrrolidine-1-carboxylate (1.20 mol) was suspended in 1.46 L of dehydrated tetrahydrofuran. While this suspension was stirred, 3.07 L of a 1.17 M tetrahydrofuran solution of borane-tetrahydrofuran complex in (3.59 mol) was added dropwise at an internal temperature of 20 to 43° C. The mixture was stirred at an internal temperature of 41 to 46° C. for 8 hours. Subsequently, the mixture was allowed to cool under stirring and then cooled in an ice bath while kept stirred. 364 mL of water was then added dropwise at an internal temperature of 15 to 25° C. Subsequently, 726 g of triethylamine was added dropwise at an internal temperature of 16 to 18° C. The mixture was then heated and stirred for 14 hours under reflux. Subsequently, the reaction mixture was allowed to cool under stirring and concentrated under reduced pressure. To the resulting residue, 1.09 L of water was added to dissolve the solid and the solution was extracted with 2.55 L of ethyl acetate. The organic layer was washed with 1.82 L of water and extracted with 1.50 L of 2 mol/L hydrochloric acid. A 2 mol/L sodium hydroxide solution (1.67 L) was then added to the aqueous layer under stirring until pH 12. The mixture was extracted with 2.55 L of ethyl acetate and the organic layer was washed with 1.82 L of 28% brine. To this layer, 255 g of anhydrous sodium sulfate was added and the mixture was stirred for 1 hour. The resulting solid was separated by filtration and washed with 0.55 L of ethyl acetate. The filtrate and the wash were combined and concentrated under reduced pressure to give 345 g of a crude product of the title compound as a faint yellow oil. This product was used in the subsequent step without further purification.

$^1$H-NMR (CDCl$_3$, 400 MHz) δ: 0.26-0.53 (4H, m), 2.06-2.21 (2H, m), 2.66 (1H, t, J=11.3 Hz), 2.95-3.09 (2H, m), 3.20 (1H, ddd, J=31.0, 15.5, 7.8 Hz), 3.65 (1H, ddd, J=16.2, 8.3, 5.3 Hz), 3.75-3.81 (1H, m), 4.10 (1H, q, J=7.3 Hz), 5.09-5.15 (2H, m), 7.28-7.43 (5H, m).

CI-MS (positive): m/z 291 [M+H]$^+$

Example 5

Synthesis of Benzyl (3S,4R)-3-cyclopropylaminomethyl-4-hydroxypyrrolidine-1-carboxylate hydrochloride

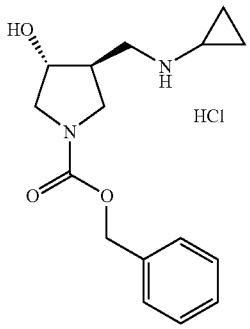

(Chemical formula 19)

4.86 L of ethyl acetate was added to 345 g of benzyl (3S,4R)-3-cyclopropylaminomethyl-4-hydroxypyrrolidine-1-carboxylate (1.20 mol) to dissolve the compound. While this solution was stirred, 1.04 L of a 10%% hydrogen chloride methanol solution was added at an internal temperature of 21° C. Following the formation of crystals (internal temperature of 20° C.), the mixture was kept stirred for 15 minutes. Subsequently, 9.72 L of diisopropyl ether was added slowly and the mixture was further stirred for 30 minutes. The resulting crystals were collected by filtration, washed with 0.52 L of ethyl acetate, and drained for 30 minutes. The product was then dried by air-blowing at 60° C. for 4 hours to give 350 g of the title compound as white powder crystals (90% yield in the 2 steps).

Melting point: 153.6-155.4° C. $^1$H-NMR (DMSO-d$_6$, 400 MHz) δ: 0.68-0.94 (4H, m), 2.29-2.45 (1H, m), 2.63-2.77 (1H, m), 2.91-3.05 (1H, m), 3.07-3.26 (3H, m), 3.52-3.66 (2H, m), 4.06 (1H, br s), 5.07 (2H, dd, J=14.2, 12.0 Hz), 5.47 (1H, br s), 7.29-7.40 (5H, m), 8.57 (2H, brs).

CI-MS (positive): m/z 291 [M+H]$^+$ $[α]_D^{24}$ 36.7 (c=0.30, methanol)

Example 6

Synthesis of benzyl (3S,4R)-3-(N-benzyl-N-cyclopropyl)aminomethyl-4-hydroxypyrrolidine-1-carboxylate

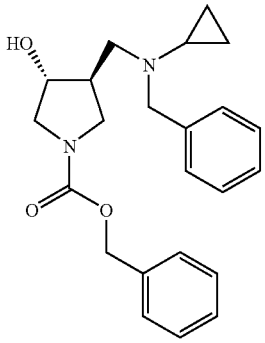

(Chemical formula 20)

942 mL of ethanol and 942 mL of purified water were added to 314 g of benzyl (3S,4R)-3-cyclopropylaminomethyl-4-hydroxypyrrolidine-1-carboxylatehydrochloride (0.96 mol) to dissolve the compound. While this solution was stirred, 178 g of sodium bicarbonate (2.11 mol) was added at an internal temperature of 27 to 29° C. 197 g of benzyl bromide (1.15 mol) was then added dropwise at an internal temperature of 25 to 27° C. and the mixture was stirred for 2 hours at an internal temperature of to 40 to 44° C. The ethanol component of the reaction mixture was concentrated under reduced pressure and the resulting residue was extracted with 1.57 L of ethyl acetate. The organic layer was washed successively with 628 mL of 2% brine and 942 mL of 28% brine and dried over anhydrous sodium sulfate. The resulting solid was separated by filtration and washed with 471 mL of ethyl acetate. The filtrate and the wash were combined and concentrated under reduced pressure to give 392 g of a crude product of the title compound as a faint yellow oil. This product was used in the subsequent step without further purification.

$^1$H-NMR (CDCl$_3$, 400 MHz) δ: 0.34-0.56 (4H, m), 1.77-1.84 (1H, m), 2.33-2.43 (1H, m), 2.54-2.72 (2H, m), 2.90-2.95 (1H, m), 3.18 (1H, ddd, J=16.4, 9.5, 5.6 Hz), 3.53-3.67 (3H, m), 3.85-3.90 (2H, m), 5.11 (2H, s), 7.24-7.40 (10H, m).

ESI-MS (positive): m/z 381 [M+H]$^+$

Example 7

Synthesis of benzyl (3S,4S)-3-(N-benzyl-N-cyclopropyl)aminomethyl-4-fluoropyrrolidine-1-carboxylate

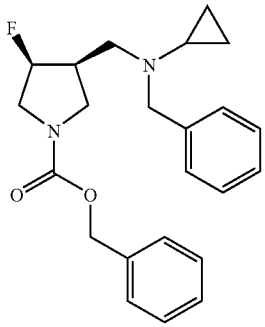

(Chemistry formula 21)

3.66 L of toluene was added to 391 g of benzyl (3S,4R)-3-(N-benzyl-N-cyclopropyl)aminomethyl-4-hydroxypyrrolidine-1-carboxylate (equivalent to 0.96 mol) to dissolve the compound. To this solution, 1,8-diazabicyclo[5.4.0]undeca-7-ene (DBU, 1.44 mol) was added. While the mixture was cooled under stirring in an ice bath, 724 g of perfluoro-1-octanesulfonylfluoride (1.44 mol) was added dropwise at an internal temperature of 2 to 10° C. The mixture was stirred at an internal temperature of 2 to 7° C. for 30 minutes. The mixture was then allowed to warm to room temperature and stirred for 2 hours. Subsequently, the reaction mixture was allowed to stand and the toluene layer (top layer) was collected. 1.83 L of toluene was added to the bottom layer and this mixture was stirred for 10 minutes. The resulting mixture was then allowed to stand and the toluene layer (top layer) was collected. The toluene layers were combined and concentrated under reduced pressure. The resulting residue was subjected to silica gel column chromatography [silica gel 60 (spherical, 63-210 μm), 3.66 kg, eluant=hexane:ethyl acetate=6:1->3:1]. The fraction containing the target product was collected and concentrated under reduced pressure to give 290 g of the title compound as a yellow oil (79% yield in the 2 steps).

$^1$H-NMR (CDCl$_3$, 400 MHz) δ: 0.36-0.50 (4H, m), 1.77-1.83 (1H, m), 2.38-2.54 (1H, m), 2.61-2.70 (1H, m), 2.85 (1H, dd, J=12.5, 6.8 Hz), 3.06 (1H, dt, J=20.2, 8.5 Hz), 3.42-3.82 (5H, m), 4.92-5.17 (3H, m), 7.21-7.37 (10H, m).

ESI-MS (positive): m/z 383 [M+H]$^+$

Example 8

Synthesis of (3R,4S)-3-cyclopropylaminomethyl-4-fluoropyrrolidine

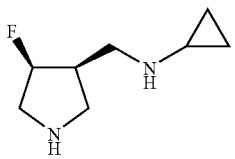

(Chemical formula 22)

2.90 L of ethanol was added to 290 g of benzyl (3S,4S)-3-(N-benzyl-N-cyclopropyl)aminomethyl-4-fluoropyrrolidine-1-carboxylate (758 mmol) to dissolve the compound. The air in the reaction system was replaced by argon. 58.0 g of 10% palladium carbon was added and argon was replaced by hydrogen. The mixture was then stirred at room temperature for 24.5 hours. Subsequently, hydrogen was replaced by argon and the catalyst was separated by filtration and washed with 290 mL of ethanol. The filtrate and the wash were combined and concentrated under reduced pressure to give 110 g of a crude product of the title compound as a yellow oil. This product was used in the subsequent step without further purification.

Example 9

Synthesis of (3R,4S)-3-cyclopropylaminomethyl-4-fluoropyrrolidine dihydrochloride

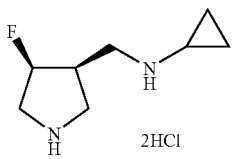

(Chemical formula 23)

360 mL of ethanol was added to 110 g of (3R,4S)-3-cyclopropylaminomethyl-4-fluoropyrrolidine (equivalent to 758 mmol) to dissolve the compound. While this solution was stirred, 1.38 L of a 10% hydrogen chloride-methanol solution was added dropwise at an internal temperature of 27 to 33° C. 1.68 L of ethyl acetate was then added dropwise for crystallization (internal temperature of 19° C.). The mixture was stirred for 10 minutes at an internal temperature of 19° C. Subsequently, 1.08 L of ethyl acetate was added dropwise at an internal temperature of 18 to 19° C. and the mixture was stirred for 30 minutes at an internal temperature of 18 to 19° C. The resulting crystals were collected by filtration and washed with 600 mL of a 2:1 mixture of ethyl acetate/methanol. The washed product was drained for 30 minutes and dried by air-blowing at 60° C. for 17 hours to give 82.7 g of a crude product as reddish white powder crystals. To the crude product (82.5 g), 0.83 L of ethanol was added and 50 mL of purified water was added dropwise at an external temperature of 60 to 70° C. to dissolve the product (internal temperature of 65° C.). The solution was allowed to cool under stirring and then cooled in a water bath while kept stirred for crystallization (internal temperature of 28.0° C.). The mixture was continuously cooled in a water bath under stirring until its internal temperature was 20° C., after which it was cooled in an ice bath under stirring for 1 hour. The crystallized product was collected by filtration at an internal temperature of 3° C. and washed with 0.25 L of ethanol. The washed product was drained for 30 minutes and air-dried to give 48.2 g of the title compound as brown powder crystals (27% yield in the 2 steps).

Melting point: 199.9-202.1° C. $^1$H-NMR (DMSO-d$_6$, 400 MHz) δ: 0.72-0.80 (2H, m), 0.90-1.07 (2H, m), 2.69-2.88 (2H, m), 3.02-3.16 (2H, m), 3.29-3.32 (2H, m), 3.41-3.64 (3H, m), 5.37-5.55 (1H, m), 9.63 (4H, br s).

CI-MS (positive): m/z 199 [M+H]$^+$ $[α]_D^{24}$-20.0 (c=0.30, distilled water)

Example 10

Synthesis of 1-benzyl 3-ethyl (3R,4S)-4-hydroxypyrrolidine-1,3-dicarboxylate

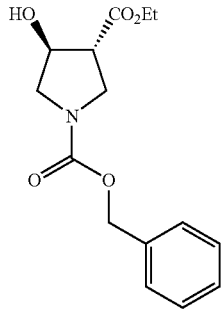

(Chemical formula 24)

43 mL of anhydrous N,N-dimethylformamide was added to 1.15 g of benzene ruthenium (II) chloride dimer (2.30 mmol) and 3.00 g of (R)-(−)-BINAP (4.82 mmol) in a stream of argon gas. The mixture was stirred in an oil bath at an external temperature of 95 to 105° C. for 10 minutes. The mixture was then allowed to cool to room temperature. Volatile materials were evaporated under reduced pressure (using a vacuum pump) in an oil bath at an external temperature of 50 to 70° C. to give a catalyst. 33.5 g of 1-benzyl 3-ethyl 4-oxopyrrolidine-1,3-dicarboxylate (115 mmol) and 68 mL of dehydrated dichloromethane were placed in an autoclave and the air in the autoclave was replaced by argon. The catalyst dissolved in 100 mL of dehydrated dichloromethane was then added and the atmosphere in the autoclave was replaced by hydrogen gas three times. The mixture was stirred under a pressurized hydrogen atmosphere (8.83 MPa) at an external temperature of 50 to 60° C. for 4 hours. Heating/stirring was stopped, and the mixture was left overnight. Subsequently, hydrogen gas was released and the mixture was transferred to a different vessel and washed with 30 mL of dehydrated dichloromethane. The mixture was then concentrated under reduced pressure and dried in vacuo at room temperature for 30 minutes to give 42.3 g of a crude product of the title compound as a dark brown oil. This product was used in the subsequent step without further purification.

$^1$H-NMR (CDCl$_3$, 400 MHz) δ: 1.27 (3H, t, J=7.3 Hz), 2.37 (1H, brs), 2.96-3.07 (1H, m), 3.33-3.40 (1H, m), 3.62-3.87 (3H, m), 4.19 (2H, q, J=7.3 Hz), 4.56-4.60 (1H, m), 5.14 (2H, s), 7.31-7.37 (5H, m).

EI-MS: m/z 293 (M)$^+$

Example 11

Synthesis of (3R,4S)-1-benzyloxycarbonyl-4-hydroxypyrrolidine-3-carboxylic acid

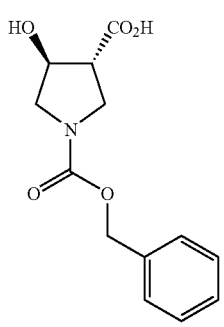

(Chemical formula 25)

42.1 g of 1-benzyl 3-ethyl (3R,4S)-4-hydroxypyrrolidine-1,3-dicarboxylate (equivalent to 114 mmol) was suspended in 330 mL of ethanol. To this suspension, 330 mL of water was added and the mixture was cooled in an ice bath. While the mixture was stirred, 6.84 g of a solution of sodium hydroxide (171 mmol) in 330 mL of water was added dropwise at an internal temperature of 5 to 10° C. and the mixture was stirred for 1 hour. Subsequently, 6.60 g of activated carbon was added and the mixture was stirred at room temperature for 30 minutes. The insoluble material was separated by filtration through Celite and washed with 110 mL of water. The filtrate and the wash were combined and ethanol (approx. 330 mL) was evaporated under reduced pressure. The resulting residue was washed twice with 200 mL of diisopropyl ether and the aqueous layer was filtered through Celite. 30.0 mL of 6 mol/L hydrochloric acid was added to the filtrate and the mixture was stirred for 10 minutes. 300 mL of ethyl acetate and 200 g of sodium chloride were added and the mixture was further stirred for 30 minutes. The organic layer was collected and washed with 300 mL of 28% brine. To this layer, 30.1 g of anhydrous sodium sulfate was added and the mixture was stirred for 30 minutes. The mixture was then filtered through a cotton plug and washed with 50 mL of ethyl acetate. The filtrate and the wash were combined and concentrated under reduced pressure. The resulting residue was dried in vacuo at room temperature for 4 hours to give 26.5 g of a crude product of the title compound as a dark brown amorphous material. This product was used in the subsequent step without further purification.

$^1$H-NMR (CDCl$_3$, 400 MHz) δ: 2.98-3.08 (1H, m), 3.32-3.39 (1H, m), 3.58-3.83 (3H, m), 4.55-4.59 (1H, m), 5.12 (2H, d, J=1.5 Hz), 7.27-7.35 (5H, m).

EI-MS: m/z 265 (M)$^+$

Example 12

Synthesis of benzyl (3R,4S)-3-(N-cyclopropyl)carbamoyl-4-hydroxypyrrolidine-1-carboxylate

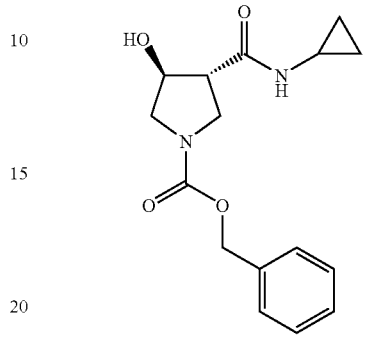

(Chemistry formula 26)

17.9 g of 1-hydroxybenzotriazole hydrate (117 mmol), 16.9 mL of cyclopropylamine (244 mmol) and 22.4 g of 1-ethyl-3-(3'-dimethylaminopropyl)carbodiimide hydrochloride (117 mmol) were successively added to a solution of (3R,4S)-1-benzyloxycarbonyl-4-hydroxypyrrolidine-3-carboxylic acid (25.9 g, 97.5 mmol) in 259 mL of dehydrated tetrahydrofuran under stirring at room temperature. The mixture was further stirred at room temperature for 5 hours. Subsequently, the reaction mixture was concentrated under reduced pressure, followed by addition of 130 mL of ethyl acetate and 260 mL of 1 mol/L hydrochloric acid and subsequent stirring for 30 minutes. The resulting crystals were collected by filtration and washed with 26 mL of ethyl acetate. The organic layer was collected and washed with 130 mL of a 10% aqueous sodium bicarbonate solution and 130 mL of 28% brine. To this layer, 39.0 g of anhydrous sodium sulfate was added and the mixture was stirred for 1 hour. The insoluble material was separated by filtration and washed with 52 mL of ethyl acetate. The filtrate was concentrated under reduced pressure. To the resulting residue, 156 mL of diisopropyl ether was added and the product was triturated. The precipitated powder was collected by filtration and washed with 39 mL of diisopropyl ether. The washed product was dried by air-blowing at room temperature for 30 minutes. 25.6 g of the resulting crystals were added to 308 mL of ethyl acetate. The mixture was heated at an external temperature of 80° C. for 25 minutes under stirring, then allowed to cool in the air for 40 minutes under stirring, then cooled in a water bath for 5 minutes under stirring at an internal temperature of 40° C., and then stirred at room temperature for 5 minutes at an internal temperature of 25° C. The precipitated powder was collected by filtration and washed with 52 mL of diisopropyl ether. The washed product was dried for 1 hour by air-blowing. Further drying the product by air-blowing at 60° C. for 16 hours gave 14.5 g of the title compound as fluffy colorless crystals (43% yield in the 3 steps).

Melting point: 132.0-133.4° C.

$^1$H-NMR (CDCl$_3$, 400 MHz) δ: 0.51 (2H, brs), 0.76-0.81 (2H, m), 2.70-2.79 (3H, m), 3.26 (1H, dd, J=7.1, 11.0 Hz), 3.52-3.62 (1H, m), 3.72-3.90 (2H, m), 4.46-4.51 (1H, m), 5.12 (2H, s), 6.04 (1H, d, J=16.1 Hz), 7.30-7.36 (5H, m).

CI-MS (positive): m/z 305 [M+H]+
$[\alpha]_D^{24}$ −24.0 (c=0.40, methanol)
Optical purity: 99.9% ee
(HPLC Conditions)
Column=CHIRAL CELL AD-RH (4.6φ×150 mm), Daicel; precolumn=INERTSIL ODS-3 (4.0φ×10 mm), GL sciences; detection wavelength=210 mm; flow rate=1.0 mL/min; mobile phase=diluted phosphoric acid (1 to 1000 fold): acetonitrile=75:25; RT=8.33 min.

Example 13

Synthesis of benzyl (3R,4S)-3-cyclopropylaminomethyl-4-hydroxypyrrolidine-1-carboxylate (Chemical formula 27)

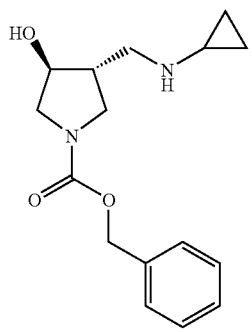

To a solution of benzyl(3R,4S)-3-(N-cyclopropyl)carbamoyl-4-hydroxypyrrolidine-1-carboxylate (14.5 g, 47.6 mmol) in 116 mL of dehydrated tetrahydrofuran, 122 mL of a tetrahydrofuran solution of borane-tetrahydrofuran complex (1.17 mol/L, 143 mmol) was added dropwise over 20 minutes at an internal temperature of 40 to 44° C. The mixture was stirred at the same temperature for 7 hours. Subsequently, the reaction mixture was cooled to an internal temperature of 25° C. or below. At an internal temperature of 15 to 25° C., 14.5 mL of water was added dropwise and the mixture was stirred for 20 minutes. At an internal temperature of 10 to 18° C., 39.8 mL of triethylamine (286 mmol) was added dropwise and the mixture was stirred for 5 minutes. The mixture was then refluxed for 15 hours. Subsequently, the mixture was allowed to cool and concentrated under reduced pressure. To the resulting residue, 44 mL of water was added and the mixture was extracted with 102 mL of ethyl acetate. The organic layer was washed with 73 mL of water and extracted with 60 mL of 2 mol/L hydrochloric acid. The aqueous layer was cooled in a water bath under stirring and 60 mL of a 2 mol/L sodium hydroxide solution was added at an internal temperature of 20 to 28° C. to adjust the pH to about 12. This mixture was extracted with 102 mL of ethyl acetate. The organic layer was washed with 73 mL of 28% brine. To the organic layer, 20.2 g of anhydrous sodium sulfate was added and the mixture was stirred for 1 hour. Subsequently, the mixture was filtered through a cotton plug and washed with 22 mL of ethyl acetate. The filtrate and the wash were combined and concentrated under reduced pressure. The product was dried at room temperature under reduced pressure for 1 hour to give 14.3 g of a crude product of the title compound as a pale yellow oil. This product was used in the subsequent step without further purification.

$^1$H-NMR (CDCl$_3$, 400 MHz) δ: 0.26-0.51 (4H, m), 2.09-2.19 (2H, m), 2.63-2.70 (1H, m), 2.93-3.07 (2H, m), 3.17-3.25 (1H, m), 3.61-3.69 (1H, m), 3.74-3.81 (1H, m), 4.04-4.09 (1H, m), 5.12 (2H, d, J=2.0 Hz), 7.30-7.37 (5H, m).
CI-MS (positive): m/z 291 [M+H]+

Example 14

Synthesis of benzyl (3R,4S)-3-cyclopropylaminomethyl-4-hydroxypyrrolidine-1-carboxylate hydrochloride (Chemical formula 28)

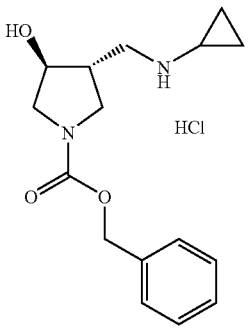

42.0 mL of a 10% hydrogen chloride-methanol solution was added dropwise to a solution of benzyl(3R,4S)-3-cyclopropylaminomethyl-4-hydroxypyrrolidine-1-carboxylate (13.9 g, equivalent to 46.4 mmol) in 195 mL of ethyl acetate under stirring at room temperature (crystallization occurred during the addition). Once crystallization took place, the mixture was stirred for 15 minutes at an internal temperature of 20 to 22° C. Subsequently, 390 mL of diisopropyl ether were added dropwise and the mixture was further stirred for 30 minutes. The resulting crystals were collected by filtration and washed with 28 mL of diisopropyl ether. The washed product was dried for 30 minutes by air-blowing and further dried at 60° C. for 2 hours under reduced pressure to give 13.5 g of the title compound as a colorless crystalline powder (92% yield in the 2 steps).

$^1$H-NMR (DMSO-d$_6$, 400 MHz) δ: 0.73 (2H, brs), 0.86 (2H, brs), 2.38 (1H, brs), 2.67-2.73 (1H, m), 2.95-3.01 (1H, m), 3.08-3.26 (3H, m), 3.52-3.66 (2H, m), 4.03-4.08 (1H, m), 5.07 (2H, d, J=2.9 Hz), 5.47 (1H, d, J=3.9 Hz), 7.30-7.40 (5H, m), 8.97 (2H, brs).
$[\alpha]_D^{24}$ −34.1 (c=0.40, methanol)

Example 15

Synthesis of benzyl (3R,4S)-3-(N-benzyl-N-cyclopropyl)aminomethyl-4-hydroxypyrrolidine-1-carboxylate (Chemical formula 29)

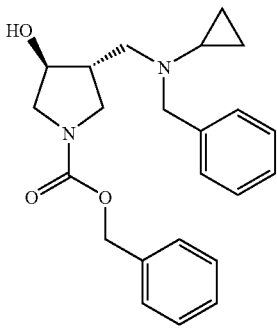

40 mL of ethanol and 40 mL of water were added to 13.5 g of benzyl(3R,4S)-3-cyclopropylaminomethyl-4-hydroxypyrrolidine-1-carboxylate hydrochloride (41.2 mmol) to dissolve the compound. To this solution, 7.62 g of sodium bicarbonate (90.7 mmol) and 8.46 g of benzyl bromide (49.5 mmol) were added and the mixture was stirred for 3 hours at an internal temperature of 40 to 45° C. Subsequently, ethanol (approx. 40 ml) was evaporated under reduced pressure and 65 mL of ethyl acetate was added to the resulting residue. This mixture was washed twice with 65 mL of 28% brine. The organic layer was dried over 15.0 g of anhydrous sodium sulfate and concentrated under reduced pressure. The resulting residue was subjected to silica gel column chromatography (silica gel 60N (spherical, neutral) 400 g, hexane:ethyl acetate=2:1→1:1). The fraction containing the target product was collected and concentrated under reduced pressure to give 16.8 g of the title compound as a colorless amorphous material (quant.).

$^1$H-NMR (CDCl$_3$, 400 MHz) δ: 0.34-0.60 (4H, m), 1.77-1.84 (1H, m), 2.31-2.45 (1H, m), 2.54-2.73 (2H, m), 2.89-2.95 (1H, m), 3.18 (1H, ddd, J=7.1, 10.7, 15.4 Hz), 3.26-3.37 (1H, m), 3.53-3.68 (3H, m), 3.84-3.91 (2H, m), 5.10 (2H, d, J=2.4 Hz), 7.24-7.36 (10H, m).

ESI-MS (positive): m/z 381 [M+H]$^+$

Example 16

Synthesis of benzyl (3R,4R)-3-(N-benzyl-N-cyclopropyl)aminomethyl-4-fluoropyrrolidine-1-carboxylate

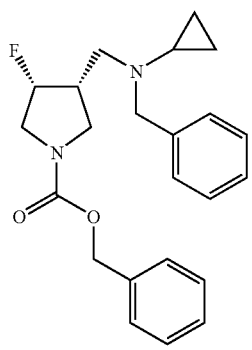

(Chemical formula 30)

9.16 mL of 1,8-diazabicyclo[5.4.0]undeca-7-ene (61.2 mmol) was added to a solution of benzyl(3R,4S)-3-(N-benzyl-N-cyclopropyl)aminomethyl-4-hydroxypyrrolidine-1-carboxylate (16.7 g, 40.8 mmol) in 167 mL of toluene. While this solution was cooled in an ice bath under stirring, 16.9 mL of perfluoro-1-octanesulfonyl fluoride (61.2 mmol) was added dropwise and the mixture was stirred at an internal temperature of 3 to 5° C. for 1 hour. The top layer was collected and the bottom layer was extracted twice with 50 mL of toluene. The toluene layers were combined and concentrated under reduced pressure. The resulting residue was subjected to silica gel column chromatography (silica gel 60N (spherical, neutral) 500 g, hexane:ethyl acetate=4:1). The fraction containing the target product was collected and concentrated under reduced pressure to give 12.7 g of the title compound as a pale yellow oil (82%).

$^1$H-NMR (CDCl$_3$, 400 MHz) δ: 0.36-0.50 (4H, m), 1.77-1.83 (1H, m), 2.37-2.56 (1H, m), 2.60-2.70 (1H, m), 2.84 (1H, dd, J=7.1, 12.5 Hz), 3.06 (1H, dt, J=10.9, 16.9 Hz), 3.50 (1H, ddt, J=3.8, 13.3, 40.1 Hz), 3.59-3.82 (4H, m), 4.92-5.08 (1H, m), 5.09-5.17 (2H, m), 7.21-7.40 (10H, m).

ESI-MS (positive): m/z 383 [M+H]$^+$

Example 17

Synthesis of (3S,4R)-3-cyclopropylaminomethyl-4-fluoropyrrolidine

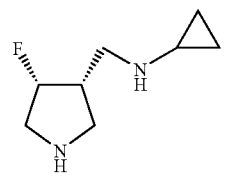

(Chemical formula 31)

1.25 g of 10% palladium carbon suspended in 25 mL of ethanol was added to a solution of benzyl(3R,4R)-3-(N-benzyl-N-cyclopropyl)aminomethyl-4-fluoropyrrolidine-1-carboxylate (12.5 g, 32.7 mmol) in 100 mL of ethanol. The air in the reaction system was replaced by argon, which was then replaced by hydrogen gas. In the hydrogen atmosphere (atmospheric pressure), the reaction mixture was stirred for 16 hours at an external temperature of 27° C. Subsequently, the atmosphere in the reaction system was replaced by argon and 1.41 g of 10% palladium carbon catalyst was added. The atmosphere in the reaction system was then replaced by hydrogen gas. In the hydrogen atmosphere (atmospheric pressure), the reaction mixture was stirred for 3 hours at an external temperature of 30° C. Subsequently, the atmosphere in the reaction system was replaced by argon and the mixture was filtered through cellulose powder, which was washed with 125 mL of ethanol. The filtrate and the wash were combined and concentrated under reduced pressure. Drying the concentrated product under reduced pressure gave 4.87 g of a crude product of the title compound as a pale yellow oil (94% yield).

$^1$H-NMR (CDCl$_3$, 400 MHz) δ: 0.30-0.47 (4H, m), 2.00 (2H, brs), 2.12-2.17 (1H, m), 2.19-2.36 (1H, m), 2.76-2.82 (2H, m), 2.96-3.13 (3H, m), 3.24 (1H, dd, J=13.7, 24.9 Hz), 5.10 (1H, dt, J=3.9, 54.7 Hz).

CI-MS (positive): m/z 159 [M+H]$^+$

Example 18

Synthesis of (3S,4R)-3-cyclopropylaminomethyl-4-fluoropyrrolidine dihydrochloride

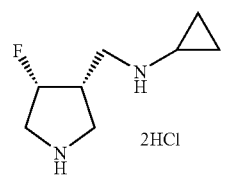

(Chemical formula 32)

To a solution of (3S,4R)-3-cyclopropylaminomethyl-4-fluoropyrrolidine (4.74 g, 30.0 mmol) in 15 mL of methanol, 60.0 mL of a 10% hydrogen chloride-methanol solution was added dropwise over 10 minutes under stirring at room temperature. The mixture was stirred for 5 minutes. 75 mL of ethyl acetate was then added dropwise over 10 minutes and the mixture was further stirred for 10 minutes. 50 mL of ethyl acetate was further added dropwise over 10 minutes and the mixture was further stirred for 30 minutes. The resulting crystals were collected by filtration and washed with 100 mL of ethyl acetate. The washed product was dried at 50° C. under reduced pressure for 4 hours to give 4.98 g of the title compound as a faint brown crystalline powder (72% yield).

$^1$H-NMR (DMSO-d$_6$, 400 MHz) δ: 0.71-0.78 (2H, m), 0.88-0.99 (2H, m), 2.67-2.88 (2H, m), 3.04 (1H, t, J=11.7 Hz), 3.14 (1H, dd, J=7.3, 13.2 Hz), 3.30 (1H, dd, J=6.3, 13.2 Hz), 3.47-3.63 (3H, m), 5.47 (1H, dt, J=2.9, 52.7 Hz), 9.63 (4H, brs).

$[α]_D^{24}$ 20.8 (c=1.00, purified water)

Example 19

Synthesis of benzyl (3S,4S)-3-(N-tert-benzyloxycarbonyl-N-cyclopropyl)aminomethyl-4-hydroxypyrrolidine-1-carboxylate (Chemical formula 33)

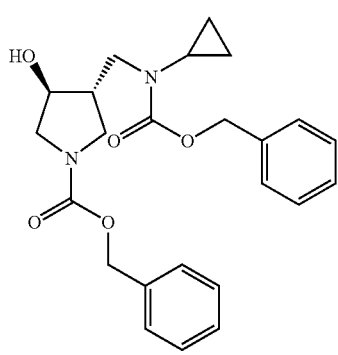

To a solution of 654 mg of benzyl (3R,4S)-3-cyclopropylaminomethyl-4-hydroxypyrrolidine-1-carboxylate hydrochloride (2.00 mmol) in 2 mL of ethanol and 2 mL of water, 504 mg of sodium bicarbonate (6.00 mmol) and 512 mg of benzyl chloroformate (3.00 mmol) were added and the mixture was stirred at room temperature for 8 hours. Subsequently, the reaction mixture was concentrated under reduced pressure and 20 mL of ethyl acetate was added to the resulting residue. This mixture was washed with 20 mL water and then 20 mL of 28% brine. The organic layer was dried over anhydrous sodium sulfate and concentrated under reduced pressure. The resulting residue was subjected to silica gel column chromatography (silica gel 60N (spherical, neutral) 50.2 g, hexane:ethyl acetate=1:2). The fraction containing the target product was collected and concentrated under reduced pressure to give 841 mg of the title compound as a colorless amorphous material (99% yield).

$^1$H-NMR (CDCl$_3$, 400 MHz) δ: 0.61-0.81 (4H, m), 2.32-2.39 (1H, m), 2.59-2.66 (1H, m), 3.14-3.31 (3H, m), 3.38-3.48 (1H, m), 3.64-3.74 (2H, m), 4.10 (1H, brs), 5.09-5.19 (4H, m), 7.30-7.40 (10H, m).

ESI-MS (positive): m/z 425 [M+H]$^+$

Example 20

Synthesis of benzyl (3S,4R)-3-(N-tert-benzyloxycarbonyl-N-cyclopropyl)aminomethyl-4-hydroxypyrrolidine-1-carboxylate (Chemical formula 34)

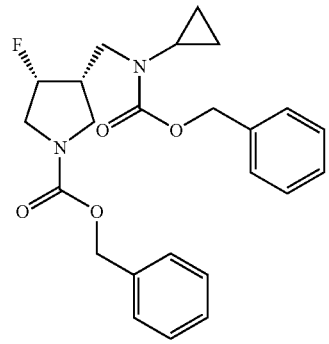

448 mg of 1,8-diazabicyclo[5.4.0]undeca-7-ene (2.94 mmol) and 1.48 g of perfluoro-1-octanesulfonyl fluoride (2.94 mmol) were added dropwise to a solution of benzyl(3R,4S)-3-(N-tert-benzyloxycarbonyl-N-cyclopropyl)aminomethyl-4-hydroxypyrrolidine-1-carboxylate (832 mg, 1.96 mmol) in 10 mL of toluene under stirring in an ice bath. The mixture was stirred for 1 hour at an external temperature of 0 to 10° C. Subsequently, the reaction mixture was concentrated under reduced pressure. The resulting residue was subjected to silica gel column chromatography (silica gel 60N (spherical, neutral) 85.0 g, hexane:ethyl acetate=2:1). The fraction containing the target product was collected and concentrated under reduced pressure to give 266 mg of the title compound as a pale yellow viscous oil (32% yield).

$^1$H-NMR (CDCl$_3$, 400 MHz) δ: 0.63-0.71 (2H, m), 0.80-0.83 (2H, m), 2.56-2.66 (2H, m), 3.21-3.31 (1H, m), 3.39-3.54 (2H, m), 3.57-3.62 (1H, m), 3.68-3.87 (2H, m), 4.99-5.18 (5H, m), 7.30-7.38 (10H, m).

ESI-MS (positive): m/z 427 [M+H]$^+$

Example 21

Synthesis of benzyl (3S,4S)-3-(N-tert-butoxycarbonyl-N-cyclopropyl)aminomethyl-4-hydroxypyrrolidine-1-carboxylate (Chemical formula 35)

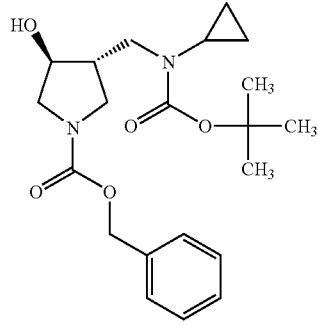

504 mg of sodium bicarbonate (6.00 mmol) and 655 mg of di-t-butyl dicarbonate (3.00 mmol) were added to a solution of benzyl(3R,4S)-3-cyclopropylaminomethyl-4-hydroxypyrrolidine-1-carboxylate hydrochloride (654 mg, 2.00 mmol) in 2 mL of ethanol and 2 mL of water. The mixture was stirred at room temperature for 8 hours. Subsequently, the reaction mixture was concentrated under reduced pressure and 20 mL of ethyl acetate was added to the resulting residue. This mixture was washed with 20 mL of water and 20 mL of 28% brine. The organic layer was dried over anhydrous sodium sulfate and concentrated under reduced pressure. The resulting residue was subjected to silica gel column chromatography (silica gel 60N (spherical, neutral) 51.1 g, hexane: ethyl acetate=1:2). The fraction containing the target product was collected and concentrated under reduced pressure to give 757 mg of the title compound as a colorless amorphous material (97% yield).

$^1$H-NMR (CDCl$_3$, 400 MHz) δ: 0.56-0.79 (4H, m), 1.46 (9H, d, J=4.4 Hz), 2.27-2.34 (1H, m), 2.51-2.55 (1H, m), 3.15-3.41 (4H, m), 3.64-3.81 (2H, m), 4.08-4.12 (1H, m), 5.13 (2H, d, J=2.9 Hz), 7.29-7.38 (5H, m).

ESI-MS (positive): m/z 391 [M+H]$^+$

Example 22

Synthesis of benzyl (3S,4R)-3-(N-tert-butoxycarbonyl-N-cyclopropyl)aminomethyl-4-fluoropyrrolidine-1-carboxylate

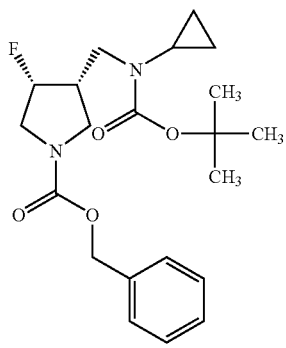

(Chemical formula 36)

436 mg of 1,8-diazabicyclo[5.4.0]undeca-7-ene (2.87 mmol) and 1.44 g of perfluoro-1-octanesulfonylfluoride (2.87 mmol) were added dropwise to a solution of benzyl(3R,4S)-3-(N-tert-butoxycarbonyl-N-cyclopropyl)aminomethyl-4-hydroxypyrrolidine-1-carboxylate (744 mg, 1.91 mmol) in 10 mL of toluene under stirring in an ice bath. The mixture was stirred for 1 hour at an external temperature of 1 to 10° C. Subsequently, the reaction mixture was concentrated under reduced pressure and the resulting residue was subjected to silica gel column chromatography (silica gel 60N (spherical, neutral) 80.1 g, hexane: ethyl acetate=2:1). The fraction containing the target product was collected and concentrated under reduced pressure to give 99.5 mg of the title compound as a pale yellow viscous oil (13% yield).

$^1$H-NMR (CDCl$_3$, 400 MHz) δ: 0.61-0.62 (2H, m), 0.76-0.78 (2H, m), 1.46 (9H, d, J=2.9 Hz), 2.49-2.64 (2H, m), 3.24-3.88 (6H, m), 5.01-5.18 (3H, m), 7.32-7.37 (5H, m).

ESI-MS (positive): m/z 393 [M+H]$^+$

INDUSTRIAL APPLICABILITY

The present invention provides an industrially advantageous process for the production of (3R,4S)-3-cyclopropylaminomethyl-4-fluoropyrrolidine or enantiomers thereof. According to the process of the present invention, the target compounds are produced via a novel production intermediate (3R,4S)-1-protected-3-cyclopropylcarbamoyl-4-hydroxypyrrolidine or enantiomers thereof.

Enabling industrially advantageous production of (3R,4S)-3-cyclopropylaminomethyl-4-fluoropyrrolidine or enantiomers thereof, the process of the present invention realizes industrially advantageous production of 10-(3-cyclopropylaminomethyl-4-fluoropyrrolidinyl)pyridobenzoxazine carboxylic acid derivatives, novel antimicrobial agents that are not only safe and potent, but are also effective against drug-resistant bacteria that can hardly be killed by conventional antimicrobial agents. Thus, high-quality pharmaceutical products using these antimicrobial agents can be provided by the present invention.

The invention claimed is:

1. A method for producing a 3-cyclopropylaminomethyl-4-fluoropyrrolidine represented by the following chemical formula (IX):

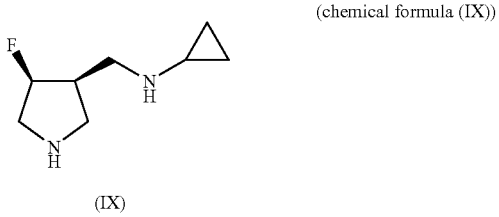

(chemical formula (IX))

(IX)

or a salt thereof, or an enantiomeric isomer thereof or a salt of the enantiomeric isomer thereof, comprising the steps of:

asymmetrically hydrogenating, with a transitional metal catalyst, a 1-protected-4-oxo-3-pyrrolidine carboxylic acid ester derivative represented by the following chemical formula (I):

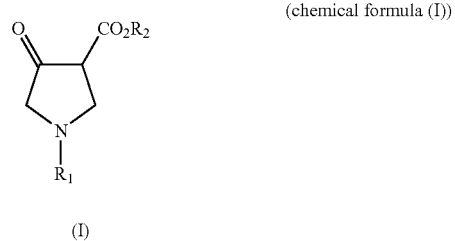

(chemical formula (I))

(I)

(wherein R$_1$ is a protecting group for the amino group; and R$_2$ is a lower alkyl group) to obtain a 4-hydroxy-3-pyrrolidine carboxylic acid ester derivative of the following chemical formula (II):

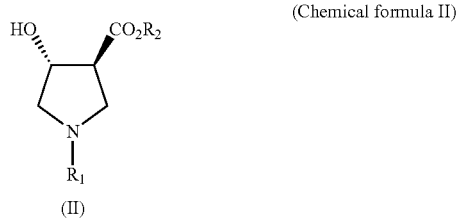

(Chemical formula II)

(II)

(wherein $R_1$ and $R_2$ are as defined above) or an enantiomeric isomer thereof;

hydrolyzing the ester group of the compound of the chemical formula (II) to obtain a 4-hydroxy-3-pyrrolidine carboxylic acid represented by the following chemical formula (III):

(Chemical formula III)

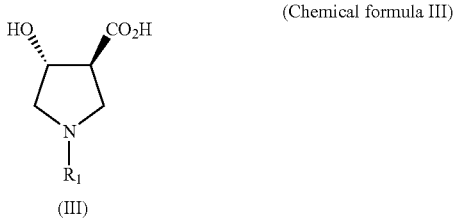

(III)

(wherein $R_1$ is as defined above) or an enantiomeric isomer thereof;

condensing the compound of the chemical formula (III) with a cyclopropylamine represented by the following chemical formula (IV):

(Chemical formula IV)

(IV)

to obtain an N-cyclopropyl-4-hydroxy-3-pyrrolidine carboxylic amide derivative represented by the following chemical formula (V):

(Chemical formula V)

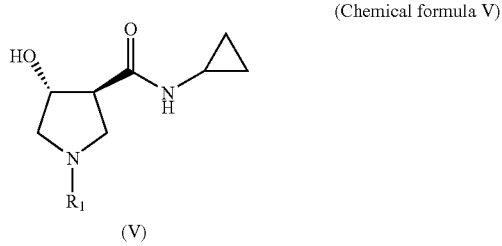

(V)

(wherein $R_1$ is as defined above) or an enantiomeric isomer thereof;

reducing the amide group of the compound of the chemical formula (V) to obtain a 4-hydroxy-3-cyclopropylamino pyrrolidine derivative represented by the following chemical formula (VI):

(Chemical formula VI)

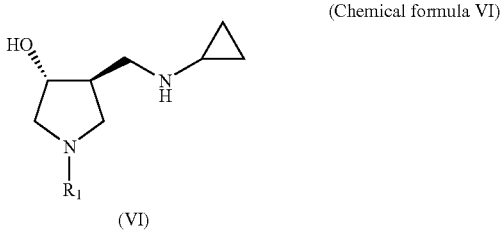

(VI)

(wherein $R_1$ is as defined above) or an enantiomeric isomer thereof;

protecting the amino group of the compound of the chemical formula (VI) to obtain a 4-hydroxy-3-cyclopropylamino pyrrolidine derivative represented by the following chemical formula (VII):

(Chemical formula VII)

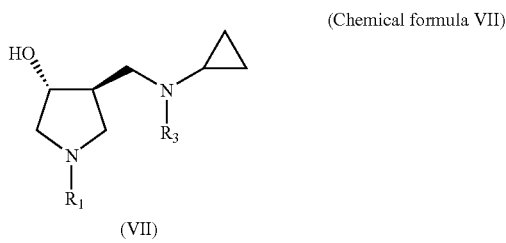

(VII)

(wherein $R_1$ is as defined above; and $R_3$ is a protecting group for the amino group and has the same definition as $R_1$) or an enantiomeric isomer thereof;

fluorinating the hydroxyl group at the 4th position of the compound of the chemical formula (VII) to obtain a 3-cyclopropylaminomethyl-4-fluoropyrrolidine derivative represented by the following chemical formula (VIII):

(Chemical formula VIII)

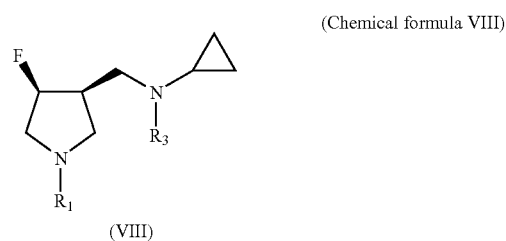

(VIII)

(wherein $R_1$ and $R_3$ are as defined above) or an enantiomeric isomer thereof; and removing the amino-protecting groups $R_1$ and $R_3$ of the compound of the chemical formula (VIII) to obtain the 3-cyclopropylaminomethyl-4-fluoropyrrolidine represented by the chemical formula (IX) or the salt thereof, or the enantiomeric isomer thereof or the salt of the enantiomeric isomer thereof.

2. The method for producing a 3-cyclopropylaminomethyl-4-fluoropyrrolidine or a salt thereof, or an enantiomeric isomer thereof or a salt of the enantiomeric isomer thereof according to claim 1, wherein the amino-protecting groups that $R_1$ and $R_3$ represent are a benzyl group, a p-methoxybenzyl group, a methoxycarbonyl group, an ethoxycarbonyl group, a propyloxycarbonyl group, an isopropyloxycarbonyl group, a butyloxycarbonyl group, an isobutyloxycarbonyl group, a tert-butyloxycarbonyl group, or a benzyloxycarbonyl group.

* * * * *